(12) United States Patent
Boada et al.

(10) Patent No.: US 10,307,139 B2
(45) Date of Patent: Jun. 4, 2019

(54) SYSTEM, METHOD AND COMPUTER-ACCESSIBLE MEDIUM FOR DIFFUSION IMAGING ACQUISITION AND ANALYSIS

(71) Applicant: New York University, New York, NY (US)

(72) Inventors: Fernando Boada, Purchase, NY (US); Steven Baete, Summit, NJ (US); Jingyun Chen, East Rutherford, NJ (US); Ricardo Otazo, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 15/419,508

(22) Filed: Jan. 30, 2017

(65) Prior Publication Data
US 2017/0220900 A1 Aug. 3, 2017

Related U.S. Application Data

(60) Provisional application No. 62/288,166, filed on Jan. 28, 2016.

(51) Int. Cl.
*A61B 5/00* (2006.01)
*A61B 8/08* (2006.01)
(Continued)

(52) U.S. Cl.
CPC .......... *A61B 8/5238* (2013.01); *A61B 5/0042* (2013.01); *A61B 5/0066* (2013.01); *A61B 5/055* (2013.01); *A61B 5/4064* (2013.01); *A61B 8/0808* (2013.01); *A61B 8/5223* (2013.01); *G01R 33/5608* (2013.01); *G06T 7/0014* (2013.01); *A61B 6/032* (2013.01); *A61B 6/501* (2013.01); *A61B 6/5217* (2013.01);
(Continued)

(58) Field of Classification Search
None
See application file for complete search history.

(56) References Cited

U.S. PATENT DOCUMENTS

2013/0278257 A1* 10/2013 Boada .................. G01R 33/561
324/309
2015/0310653 A1* 10/2015 Knoll .................... G06T 11/003
382/131

OTHER PUBLICATIONS

High definition fiber tracking for assessment of neurological deficit in a case of traumatic brain injury: Finding and Visualizi . . . , by Shin et al., Neurosurgery Mar. 2012, 1062-1069., Mar. 2012.*

(Continued)

*Primary Examiner* — Vikkram Bali
(74) *Attorney, Agent, or Firm* — Hunton Andrews Kurth LLP

(57) ABSTRACT

Exemplary system, method and computer-accessible medium for determining a difference(s) between two sets of subjects, can be provided. Using such exemplary system, method and computer-accessible medium, it is possible to receive first imaging information related to a first set of subjects of the two sets of the subjects, receive second imaging information related to a second set of subjects of the two sets of subjects, generate third information by performing a decomposition procedure(s) on the first imaging information and the second information, and determine the difference(s) based on the third information.

16 Claims, 16 Drawing Sheets

(51) Int. Cl.
| | |
|---|---|
| A61B 5/055 | (2006.01) |
| G01R 33/56 | (2006.01) |
| G06T 7/00 | (2017.01) |
| A61B 6/00 | (2006.01) |
| G01R 33/563 | (2006.01) |
| A61B 6/03 | (2006.01) |

(52) U.S. Cl.
CPC ...... *A61B 6/5229* (2013.01); *G01R 33/56341* (2013.01); *G06T 2207/10092* (2013.01); *G06T 2207/30016* (2013.01)

(56) References Cited

OTHER PUBLICATIONS

Wedeen, Van J. et al., "The Geometric Structure of the Brain Fiber Pathways," Science, vol. 335, pp. 1628-1634, Mar. 30, 2012.
Fernandez-Miranda, Juan C. et al., "High-Definition Fiber Tractography of the Human . . . ," Neurosurgery, vol. 71, No. 2, pp. 430-453, Aug. 2012.
Candes, Emmanuel J. et al., "Robust Principal Component Analysis? ," Journal of the ACM, vol. 58, No. 3, Article 11, pp. 1-37, May 2011.
Otazo, Ricardo et al., "Low-Rank Plus Sparse Matrix Decomposition for Accelerated . . . ," Magnetic Resonance in Medicine, vol. 73, pp. 1125-1136, 2015.
Baete, Steven H. et al., "Radial q-Space Sampling for DSI," Magnetic Resonance in Medicine, vol. 76, pp. 769-780, 2016.
Baete, Steven H. et al., "Accelerated Radial Diffusion Spectrum Imaging Using . . . ," Magnetic Resonance in Medicine, pp. 1-11, 2017.
Yeh, Fang-Cheng et al., "Diffusion MRI Connectometry Automatically Reveal Affected . . . ," NeuroImage: Clinical, vol. 2, pp. 912-921, 2013.
Yeh, Fang-Cheng et al., "Connectometry: A Statistical Approach Harnessing . . . ," NeuroImage, vol. 125, pp. 162-171, 2016.
Yeh, Fang-Cheng et al., "Generalized q-Sampling Imaging," IEEE Transactions on Medical Imaging, vol. 29, No. 9, pp. 1626-1635, Sep. 2010.
Shen, Bo et al., "High-Definition tDCS Alters Impulsivity in a Baseline-Dependent Manner," NeuroImage, vol. 143, pp. 343-352, 2016.
Chen, Yu-Jen et al., "Automatic Whole Brain Tract-Based Analysis Using Predefined . . . ," Human Brain Mapping, vol. 36, pp. 3441-3458, 2015.
Jahanshad, Neda et al., "Seemingly Unrelated Regression Empowers Detection . . . ," Neurobiology of Aging, vol. 36, pp. S103-S112, 2015.
Setsompop, K. et al., "Improvising Diffusion MRI Using Simultaneous Multi-Slice . . . ," NeuroImage, vol. 63, pp. 569-580, 2012.
Setsompop, Kawin et al., "Blipped-Controlled Aliasing in Parallel Imaging . . . ," Magnetic Resonance in Medicine, vol. 67, pp. 1210-1224, 2012.
Klein, Stefan et al., "elastix: A Toolbox for Intensity-Based . . . ," IEEE Transactions on Medical Imaging, vol. 29, No. 1, pp. 196-205, Jan. 2010.
Callaghan, P.T., "Principles of Nuclear Magnetic Resonance Microscopy," Magnetic Resonance in Chemistry, vol. 33, p. 322, 1995.
Basser, Peter J. et al., "Microstructural and Physiological Features of Tissues . . . ," Journal of Magnetic Resonance, Series B, vol. 111, pp. 209-219, 1996.
Tuch, David S. et al., "High Angular Resolution Diffusion Imaging Reveals . . . ," Magnetic Resonance in Medicine, vol. 48, pp. 577-582, 2002.
Wedeen, Van J. et al., "Mapping Complex Tissue Architecture with Diffusion Spectrum . . . ," Magnetic Resonance in Medicine, vol. 54, pp. 1377-1386, 2005.
Reese, Timothy G. et al., "Halving Imaging Time of Whole Brain Diffsion Spectrum . . . ," Journal Magn. Reson. Imaging, vol. 29, No. 3, pp. 1-11, Mar. 2009.
Tuch, David S. "Q-Ball Imaging," Magnetic Resonance in Medicine, vol. 52, pp. 1358-1372, 2004.
Liu, I-Chao et al., "The Microstructural Integrity of the Corpus Callosum and Associate . . . ," Psychiatry Research: Neuroimaging, vol. 184, pp. 128-134, 2010.
Jarbo, Kevin et al., "In Vivo Quantification of Global Connectivity in the Human . . . ," NeuroImage, vol. 59, pp. 1988-1996, 2012.
Kuo, Li-Wei et al., "Optimization of Diffusion Spectrum Imaging and q-Ball Imaging . . . ," NeuorImage, vol. 41, pp. 7-18, 2008.
Blaimer, Martin et al., "Multiband Phase-Constrained Parallel MRI," Magnetic Resonance in Medicine, vol. 69, pp. 974-980, 2013.
Whitcher, Brandon et al., "Statistical Group Comparison of Diffusion Tensors . . . ," Magnetic Resonance in Medicine, vol. 57, pp. 1065-1074, 2007.
Smith, Stephen M. et al., "Tract-Based Spatial Statistics: Voxelwise Analysis of . . . ," NeuorImage, vol. 31, pp. 1487-1505, 2006.
Jbabdi, Saad et al., "Crossing Fibres in Tract-Based Spatial Statistics," NeuroImage, vol. 49, pp. 249-256, 2010.
Zhang, Hui et al., "A Tract-Specific Framework for White Matter Morphometry Combining . . . ," Medical Image Analysis, vol. 14, pp. 666-673, 2010.
Jeurissen, Ben et al., "Investigating the Prevalence of Complex Fiber Configurations . . . ," Human Brain Mapping, vol. 34, pp. 2747-2766, 2013.
Bach, Michael et al., "Methodological Considerations on Tract-Based Spatial . . . ," NeuroImage, vol. 100, pp. 358-369, 2014.
Raffelt, David A. et al., "Connectivity-Based Fixel Enhancement: Whole-Brain . . . ," NeuroImage, vol. 117, pp. 40-55, 2015.
Raffelt, David et al., "Apparent Fibre Density: A Novel Measure for the Analysis . . . ," NeuoImage, vol. 59, pp. 3976-3994, 2012.
Mitra, Jhimli et al., "Statistical Machine Learning to Identify Traumatic Brain . . . ," NeuroImage, vol. 129, pp. 247-259, 2016.
Smith, Stephen M. et al., "Threshold-Free Cluster Enhancement: Addressing Problems . . . ," NeuroImage, vol. 44, pp. 83-98, 2009.
Jones, Derek K. et al., "White Matter Integrity, Fiber Count, and Fallacies: The Do's . . . ," NeuroImage, vol. 73, pp. 239-254, 2013.
Reveley, Colin et al., "Superficial White Matter Fiber Systems Impede Detection . . . ," PNAS, pp. E2820-E2828, May 11, 2015.
Thomas, Cibu et al., "Anatomical Accuracy of Brain Connections Derived . . . ," PNAS, vol. 111, No. 46, pp. 16574-16579, Nov. 18, 2014.
Lepore, Natasha et al., "A Multivariate Group-Wise Genetic Analysis of White . . . ," Diffusion MRI Workshop at MICCAI, pp. 1-11, 2010.
Zhou, Xiaowei et al., "Low-Rank Modeling and its Applications in Image Analysis," arXiv:1401.3409v3 [cs.CV], pp. 1-35, Oct. 23, 2014.
Lin, Zhouchen "A Review on Low-Rank Models in Data Analysis," AIM's Journals, pp. 1-23, 2016.
Chandrasekaran, Venkat et al., "Rank-Sparsity Incoherence for Matrix Decomposition*," SIAM J. Optim., vol. 21, No. 2, pp. 572-596, 2011.
Tourier, Donald J. et al., "Direct Estimation of the Fiber Orientation Density . . . ," NeuroImage, vol. 23, pp. 1176-1185, 2004.
Peng, Yigang et al., "RASL: Robust Alignment by Sparse and Low-Rank Decomposition . . . ," IEEE, vol. 34, pp. 763-770, 2010.
Bouwmans, Thierry et al., "Robust PCA Via Principal Component Pursuit . . . ," Computer Vision and Image Understanding, vol. 122, pp. 22-34, 2014.
Gao, Hao et al., "Compressive Diffusion MRI—Part 1: Why Low-Rank?," Proc. Intl. Soc. Mag. Reson. Med., vol. 21, p. 0610, 2013.
Gao, Hao et al., "Robust Principal Component Analysis-Based Four-Dimentional . . . ," Phys. Med. Biol., vol. 56, pp. 3181-3198, 2011.
Yuan, Xiaoming et al., "Sparse and Low-Rank Matrix Decomposition Via Alternating . . . ," Methods Optimization Online, pp. 1-11, Nov. 2009.
Lin, Zhouchen et al., "The Augmented Lagrange Multiplier Method for Exact . . . ," arXiv:1009.5055v3 [math.OC], pp. 1-23, Oct. 18, 2013.

(56) References Cited

OTHER PUBLICATIONS

Nichols, Thomas E. et al., "Nonparametric Permutation Tests for Functional Neuroimaging: . . . " Human Brain Mapping, vol. 15, pp. 1-25, 2001.
Winkler, Anderson M. et al., "Permutation Inference for the General Linear Model," NeuroImage, vol. 92, pp. 381-397, 2014.
Cohen-Adad, Julien et al., "Quality Assessment of High Angular Resolution Diffusion . . . ," Journal of Magenetic Resonance Imaging, vol. 33, pp. 1194-1208, 2011.
Baete, Steven et al., "Fast, Whole Brain Radial Diffusion Spectrum Imaging (RDSI) Via Simultaneous Multi Slice Excitation," Proc. Intl. Soc. Mag. Reson. Med, vol. 23, p. 2539, 2015.
Yeh, Fang-Cheng et al., "Connectometry: A Statistical Approach Harnessing the Analytical Potential of the Local Connectome," NeuroImage, 2015 [Internet Address] http://dx.doi.org/10.1016/j.neuroimage.2015.10.053.
Callaghan, Paul T. "Principles of Nuclear Magnetic Resonance Microscopy," Oxford: Oxford University Press, 1993.
Baete, Steven et al., "Accelerated Radial Diffusion Spectrum Imaging using a multi-echo stimulated echo diffusion sequence," In Proc Intl Soc Magn Reson Med, vol. 22, p. 88, 2014.
Peng, Yigang et al., "RASL: Robust Alignment by Sparse and Low-Rank Decomposition for Linearly Correlated Images," IEEE Trans Pattern Anal. and Mach. Int., vol. 34, pp. 2233-2246, 2012.

* cited by examiner

Figure 9A  Figure 9C  Figure 9E  Figure 9G
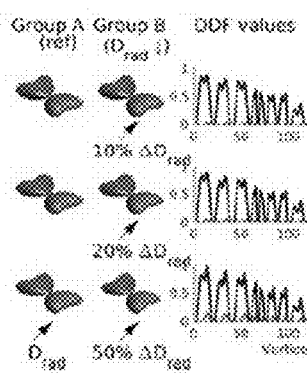
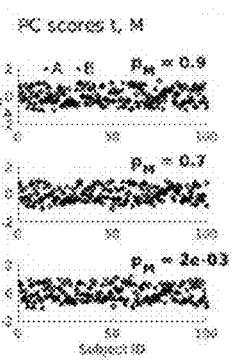
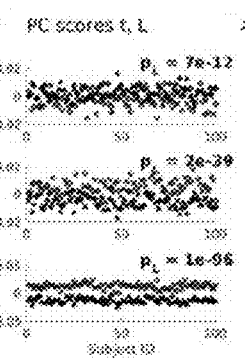
Figure 9B  Figure 9D  Figure 9F Figure 11A
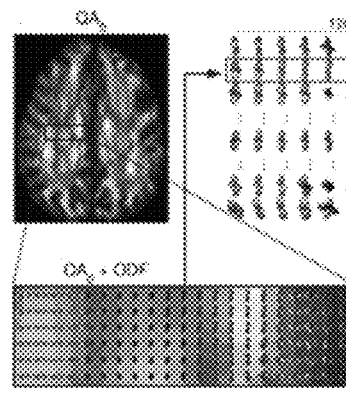
Figure 11C
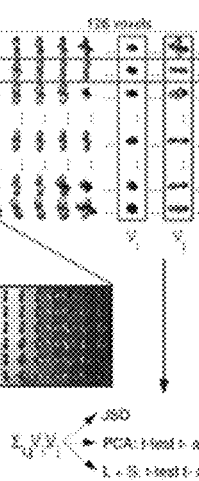
Figure 11D
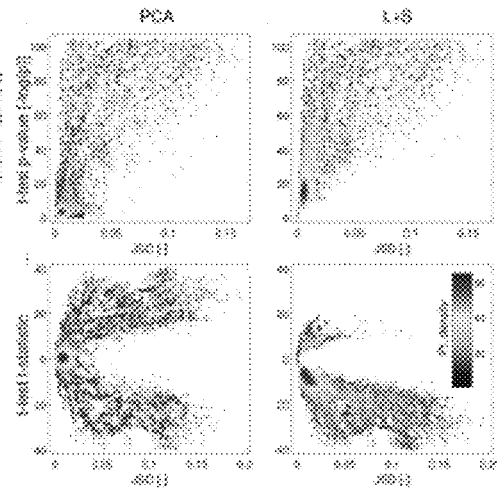
Figure 11B
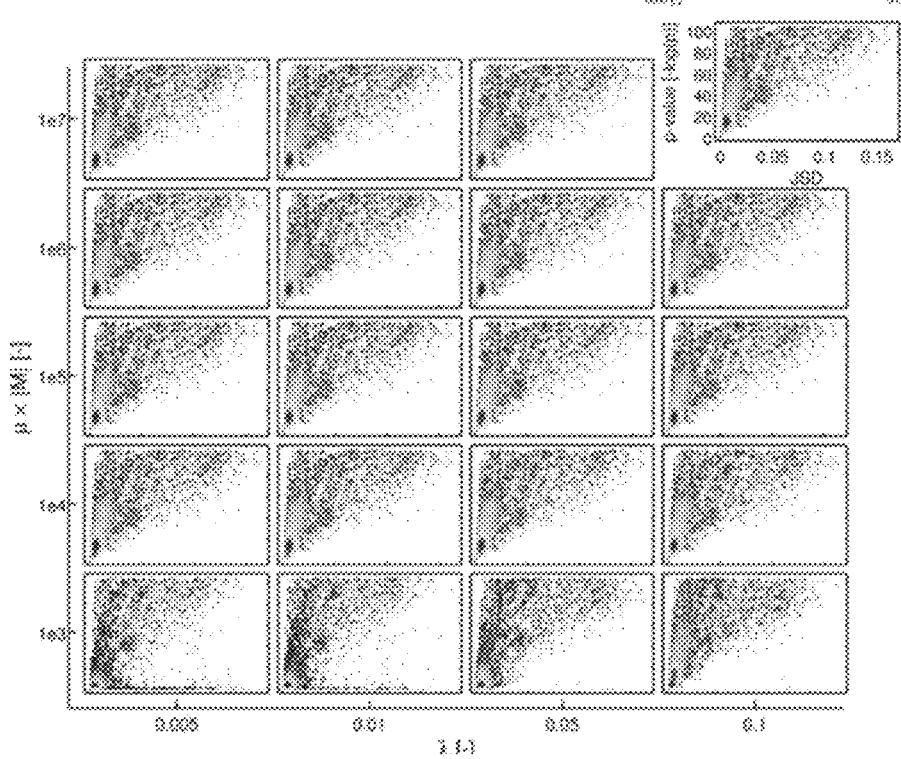
Figure 11E

SYSTEM, METHOD AND COMPUTER-ACCESSIBLE MEDIUM FOR DIFFUSION IMAGING ACQUISITION AND ANALYSIS

CROSS-REFERENCE TO RELATED APPLICATION(S)

This application relates to and claims priority from U.S. Patent Application No. 62/288,166, filed on Jan. 28, 2016, the entire disclosure of which is incorporated herein by reference.

STATEMENT REGARDING FEDERALLY SPONSORED RESEARCH

This invention was made with government support under Grant Nos. R01CA111996, R01NS082436 and R01MH00380, awarded by the National Institute of Health. The government has certain rights in the invention.

FIELD OF THE DISCLOSURE

The present disclosure relates to diffusion imaging acquisition, and more specifically, to exemplary embodiments of exemplary system, method and computer-accessible medium for diffusion imaging acquisition and analysis.

BACKGROUND INFORMATION

Diffusion Spectrum Imaging ("DSI") (see, e.g., Reference 1) provides a robust estimation of intra-voxel fiber tract crossings (see, e.g., Reference 2), facilitating accurate modeling of the white-matter wiring of the human brain. Higher order diffusion acquisitions, such as DSI (see, e.g., Reference 9), are invaluable tools for the non-invasive study of white matter connectivity. Indeed, complex intra-voxel fiber crossings are captured in an Orientation Distribution Function ("ODF"). (See, e.g., References 9 and 10). Additionally, recent sequence improvements have reduced acquisition times, making DSI a practical tool for neuroscience research (see, e.g., References 11 and 12). This evolution has highlighted the need for a robust methodology for statistical analysis of group ODF datasets.

One previous method contrasts subject ODF values to those of a normal population (see, e.g., Reference 13); however this prior approach is limited to predetermined skeletons of fiber directions. Other methods focus on the connectome level, evaluating differences in structural connections on a local (see, e.g., Reference 14) or global (see, e.g., Reference 15) level, thus possibly missing more subtle differences in diffusion behavior captured in the ODF.

Diffusion weighted ("DW") magnetic resonance imaging ("MRI") samples the diffusive displacement of water, and its interactions with cellular structures, such as axon membranes in in vivo white matter. (See, e.g., References 22 and 23). By encoding the anisotropic tissue micro-structure, DW MRI provides insight in the complex white matter tract architecture. Highly detailed High Angular Resolution Diffusion Imaging ("HARDI"), (see, e.g., Reference 24)) methods such as DSI (see, e.g., References 22 and 25-27) and Q-ball imaging (see, e.g., Reference 28), facilitate the capture of the complex fiber crossings in each voxel (see, e.g., References 26 and 29) in ODF. (See, e.g., Reference 22). Combinations of these voxel-wise ODFs over the brain supplies tractography procedures with an estimate of the connection infrastructure of the brain. While tractography procedures continue to evolve, the connection information they provide has been successfully used for depicting changes in brain research (see, e.g., References 30 and 31) and pathologically relevant conditions. (See, e.g., Reference 29).

Widespread adoption of HARDI datasets in group studies has been hindered by the long acquisition times needed for the large number of q-space samples utilized for sufficient angular resolution. (See, e.g., References 32 and 33). Recent developments in simultaneous multi-slice or multiband procedures (see, e.g., References 34 and 35) and sequence design (see, e.g., References 36-38) have led to data acquisition times that, for the first time, make HARDI a viable and practical tool for clinical applications and neuroscience research. This evolution has highlighted the need for a robust methodology for statistical analysis of group ODF data sets.

A number of methods have previously been proposed to identify and study differences in the diffusion signals of groups of subjects. Diffusion-specific Voxel-Based analysis ("VBA") methods register quantitative diffusion measures for the whole brain (see, e.g., Reference 39) or project them on a tract skeleton, for example, Tract-Based spatial Statistics ("TBSS") (see, e.g., References 40 and 41) or surface. (See, e.g., Reference 42). Most of these approaches are based on information gained from Diffusion Tensor Imaging ("DTI") (see, e.g., Reference 23), an incomplete representation of the complex intra-voxel crossings. (See, e.g., Reference 43). This is partially mitigated by an extension of the TBSS-method accommodating two crossing fibers. (See, e.g., Reference 41). Nevertheless, the focus of these methods on DTI makes them ill-suited to fully exploit the much higher dimensionality of the ODFs. In addition, the projection based methods suffer from inaccurate tract representations and projections. (See, e.g., References 44 and 45).

Other methods use tractography results to identify structurally connected fiber populations globally or locally. (See, e.g., References 45-49). The resulting connectivity matrices can then be used directly for statistical tests (see, e.g., References 46, 47 and 50) or the tractograms can inform tract-specific smoothing (see, e.g., References 45 and 48) and enhancement of statistical maps along the tracts (see, e.g., References 45, 48 and 49) using Threshold-Free Cluster Enhancement approaches ("TFCE") (see, e.g., Reference 51). While these tractography based methods are powerful, they suffer from problems related to imperfections in the tractography (see, e.g., References 52-54); some limit the identified fiber directions to a predefined template (see, e.g., Reference 49) and they generally miss more subtle differences in diffusion behavior captured in the ODF.

Various methods for group difference identification in diffusion Mill studies capitalize on the information contained in the ODFs registered to a common atlas. Early work used voxel-wise whole brain multivariate statistics on the coefficients of the ODFs spherical harmonics representations. (See, e.g., Reference 55). The first work to mine the high dimensionality of the whole ODF rather than a representation, applied Principal Component Analysis ("PCA") to identify the defining ODF features in each voxel in a whole brain group analysis. (See, e.g., Reference 47). In each voxel, the Principal Components ("PC") represent an orthogonal basis of ODF features that are common within, common between or different between subject cohorts. Statistical analysis of the weights of the PCs, the PC-scores, then informs the significance of group differences. (See, e.g., Reference 47). However, PCA is sensitive to outliers and can be easily corrupted by the individual variability of subjects (see, e.g., References 56 and 57), reducing the power of the statistical test.

Thus, it may be beneficial to provide an exemplary system, method and computer-accessible medium for diffusion imaging acquisition and analysis which can overcome at least some of the deficiencies described herein above.

SUMMARY OF EXEMPLARY EMBODIMENTS

An exemplary system, method and computer-accessible medium for determining a difference(s) between two sets of subjects, can be provided, which can include, for example receiving first imaging information related to a first set of subjects of the two sets of the subjects, receiving second imaging information related to a second set of subjects of the two sets of subjects, generating third information by performing a decomposition procedure(s) on the first imaging information and the second imaging information, and determining the difference(s) based on the third information.

In some exemplary embodiments of the present disclosure, the first imaging information can include a plurality of first images, and a particular first image of the first images can correspond to a particular first subject in the first set of subjects, and the second imaging information can include a plurality of second images, and a particular second image of the second images can correspond to a particular second subject in the second set of subjects. A matrix(es) can be generated based on the first imaging information and the second imaging information, and the third information can be generated by decomposing the matrix(es) into a feature matrix(es) and a residual matrix(es) using the decomposition procedure(s). The first set of subjects can be different than the second set of subjects. The decomposition procedure(s) can be a low rank plus sparse (L+S) decomposition procedure. A first matrix(es) can be generated based on the first imaging information and second matrix(es) can be generated based on the second imaging information.

In certain exemplary embodiments of the present disclosure, columns of the first matrix(es) can correspond to particular first subjects in the first set of subjects and rows of the first matrix(es) can correspond to features of the particular first subjects, and columns of the second matrix(es) can correspond to particular second subjects in the second set of subjects and rows of the second matrix(es) can correspond to features of the particular second subjects. The third information can be generated by decomposing (i) the first matrix(es) into a first feature matrix(es) and a first residual matrix(es) using the L+S decomposition procedure, and (ii) the second matrix(es) into a second feature matrix(es) and a second residual matrix(es) using the L+S decomposition procedure.

In some exemplary embodiments of the present disclosure, the difference(s) can be based on the first feature matrix(es) and the second feature matrix(es). The difference(es) can be determined by comparing the first feature matrix(es) to the second feature matrix(es) on a voxel by voxel basis. The first residual matrix(es) can include outliers from the first set of subjects and the second residual matrix(es) can include outliers from the second set of subjects. The first information and the second imaging information can be co-registered and mapped to an atlas(es). The first imaging information and the second imaging information can be generated, and they can include magnetic resonance imaging information, computed tomography imaging information, optical coherence tomography imaging information, ultrasound imaging information or Optical Frequency Domain Reflectometry imaging information.

In certain exemplary embodiments of the present disclosure, the first imaging information can include a plurality of first images of brains of the first set of subjects, and the second imaging information can include a plurality of second images of brains of the second set of subjects. The difference(s) can include a presence or absence of a traumatic brain injury. The difference(s) can include an Orientation Distribution Function group difference.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIGS. 9A-9G is a set of exemplary images and graphs illustrating simulations of the detection of the reduction in Radial Diffusivity of one fiber in a pair of fiber crossings according to an exemplary embodiment of the present disclosure;

FIG. 11A is an exemplary diagram illustrating an evaluation of Orientation Distribution Function group difference detection on groups of registered in vivo Orientation Distribution Functions according to an exemplary embodiment of the present disclosure;

FIG. 11B is an exemplary diagram illustrating an evaluation of Orientation Distribution Functions group differences obtained from a segment of a brain according to an exemplary embodiment of the present disclosure;

FIG. 11C is an exemplary matrix of reorganized Orientation Distribution Functions according to an exemplary embodiment of the present disclosure;

FIG. 11D is a set of exemplary charts illustrating the Jensen-Shannon Divergence according to an exemplary embodiment of the present disclosure;

FIG. 11E is a set of exemplary graphs illustrating the impact of the choice of the parameters $\lambda$ and $\mu$ of the L+S-decomposition on the detection of significant Orientation Distribution Functions group differences according to an exemplary embodiment of the present disclosure;

Figure 1:
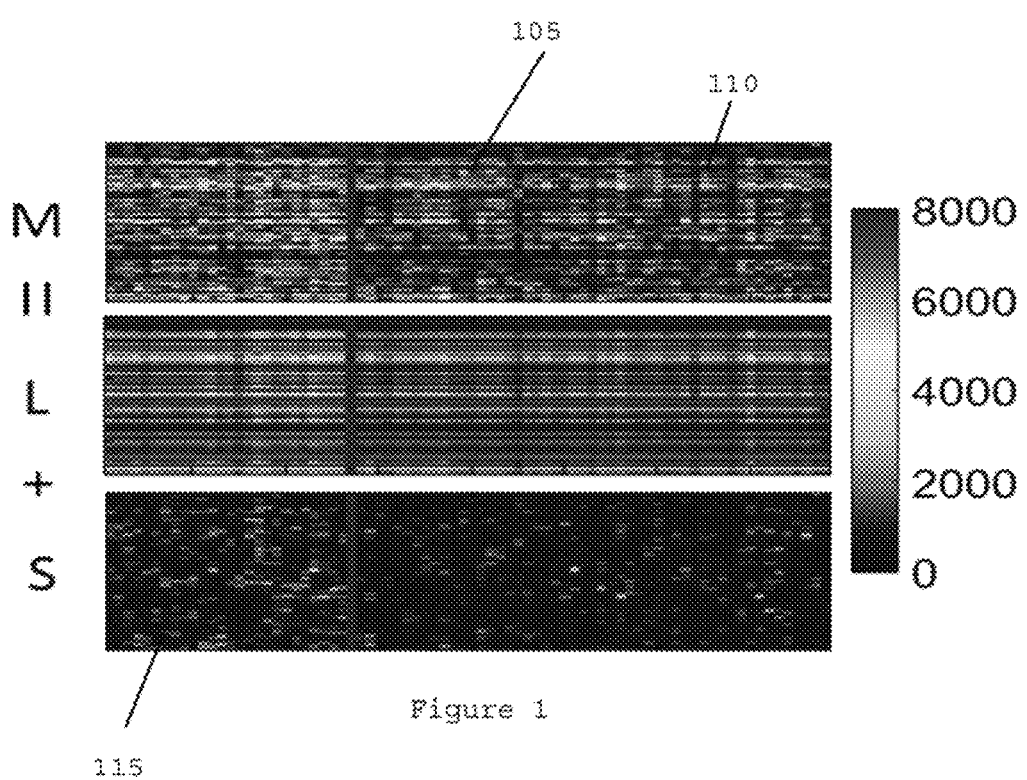
FIG. 1 is an exemplary set of exemplary feature matrices showing the effect of Low-Rank plus Sparse decomposition according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary system, method and computer-accessible medium, according to an exemplary embodiment of the present disclosure, relates to diffusion imaging acquisition and analysis. For example, the exemplary system, method and computer-accessible medium, according to an exemplary embodiment of the present disclosure, can be used to assess the neurological condition of a subject (e.g., traumatic brain injury, concussion, post-traumatic stress disorder etc.). A population or group of subjects can be assessed/evaluated, and the information can be used at a later time in order to diagnose an individual subject. Thus, the exemplary evaluation of groups of subjects can be used as reference information/data for diagnosing an individual subject.

Low rank plus sparse (L+S) decomposition is a non-linear operation that facilitates separation (e.g., optimal separation) of correlated components within a model matrix. The exemplary system, method and computer-accessible medium, according to an exemplary embodiment of the present disclosure, can use the exemplary L+S procedure for the detection of correlation between the columns of a matrix. This can facilitate the use of L+S for detecting similarities between groups of data collected during population studies. Population studies can often be hindered by a high degree of biological variation within the sample (e.g., outliers), which can compromise the ability to detect statistically significant differences between populations of subjects (e.g., Alzheimer's disease subjects vs. Aged Matched Controls). Thus, the exemplary system, method and computer-accessible medium, according to an exemplary embodiment of the present disclosure, can use the L+S procedure to separate the outliers' features (e.g., because they are sparse) from the population's mean and, thus, increase the ability to find differences between populations. This can be accomplished by performing a L+S decomposition for each population group and then performing the statistical test of interest between the L components from each group.

The exemplary system, method and computer-accessible medium, according to an exemplary embodiment of the present disclosure, can utilize the L+S decomposition to evaluate differences in the brain's structural connectivity between post-traumatic stress disorder subjects and controls. During this exemplary analysis, the diffusion scans of each group can be "spatially normalized" to an atlas, and the resulting scans can be used as the columns of a feature matrix (e.g., one matrix per group). The feature matrices can then be decomposed using the L+S procedure and the L components for each group can then be evaluated for differences using an exemplary pixel-wise statistical tests. During simulated results (e.g., where the ground truth can be known) the statistical significance can be reliably increased by two orders of magnitude using the exemplary system, method and computer-accessible medium.

Various diffusion procedures can be used, which can include, for example, (i) diffusion spectrum imaging, diffusion weighted imaging, diffusion tensor imaging and/or diffusion kurtosis imaging. The exemplary system, method and computer-accessible medium, according to an exemplary embodiment of the present disclosure, can incorporate an exemplary denoising procedure such as, for example, L+S decomposition. Nonetheless, it should be understood that other suitable denoising procedures can also be used. The exemplary system, method and computer-accessible medium, according to an exemplary embodiment of the present disclosure, can be used for subjects with and without traumatic brain injury ("TBI"). The L+S decomposition procedure can be used to identify cohort-specific connectivity signatures that are robust to outlier biases. (See, e.g., References 3 and 4).

Exemplary Method

For example, 78 subjects participated in an exemplary study, including 51 TBI (e.g., 48 male/3 female, 32±7 (e.g., 21-51) years old) and 27 healthy controls (e.g., 21 male/6 female, 29±5 (e.g., 22-44) years old). DSI datasets were acquired using a twice-refocused spin Echo Planar Imaging ("EPI") sequence (e.g., 3 T Skyra, Siemens; 20-ch head coil; TR/TE=2600/114 ms, 52 slices, 2.2 mm isotropic), parallel imaging (e.g., 2×, GRAPPA) and simultaneous multi-slice acceleration of 4, 10:49 min; max b=4000, Radial q-space sampling (e.g., 59 radial lines, 4 shells). (See e.g., Reference 5). Images were corrected for susceptibility, eddy currents and movement, and then registered to the MNI152-2 mm atlas. Whole brain tractography was performed on the registered DSI datasets using DSI Studio (see e.g., Reference 6) (e.g., seed number=1e6, turning angle=60, FA threshold=0.01, step size=1.1, smoothing=0.2, min length=10, max length=500, tracking method=RK4). Structural connectivity matrices, based on fiber numbers and average fiber lengths, were computed among 268 seed regions of similar sizes defined by data-driven procedures. (See e.g., Reference 7). To test the group differences on structural connectivity, the upper triangle entries of the structural connectivity matrices were rearranged into feature vectors, and lined up by subjects to form the feature matrix. A mask was applied to filter invalid features (e.g. all zero across the subjects). Two-sample t-tests were first performed on the feature matrix ("M"), then on the Low-Rank matrix L of M.

Exemplary Results

The exemplary effect of the application of the L+S decomposition procedure is illustrated in FIG. 1. The original matrix M (109) (e.g., rows are features and columns are subjects) can be decomposed into a matrix L (110) with minimum rank, and the residual matrix S (115) containing sparse noise (e.g., outliers).

Figure 2:
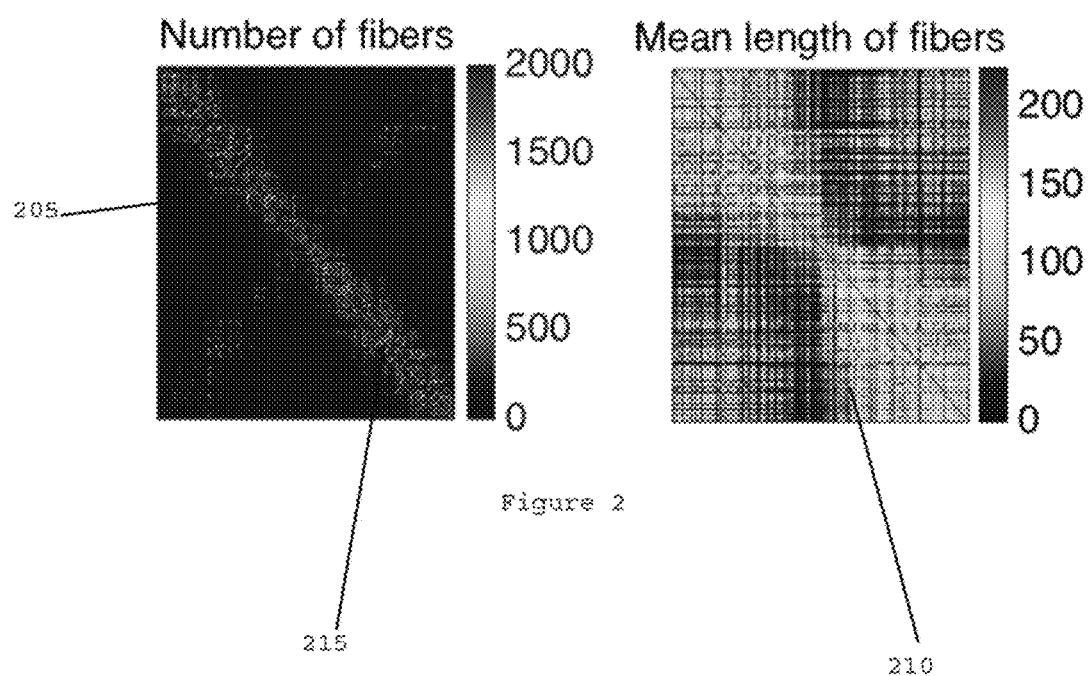
FIG. 2 is an exemplary set of the exemplary feature matrices illustrating the average connectivity matrices over all subjects according to an exemplary embodiment of the present disclosure.

The average connectivity matrices of fiber numbers (205) and fiber lengths (210) are shown in FIG. 2. Most of the connections occurred along the upper-left-lower-right diagonal line (215) of the fiber numbers matrix 205, which can be ROI couples close to each other. Fewer connections accrued on the upper-right and lower-left corner of the fiber numbers matrix 205, which can be ROI couples from opposite hemispheres. This exemplary distribution of connection distances can also be reflected by the connectivity matrix of the fiber lengths matrix 210.

Figure 3:
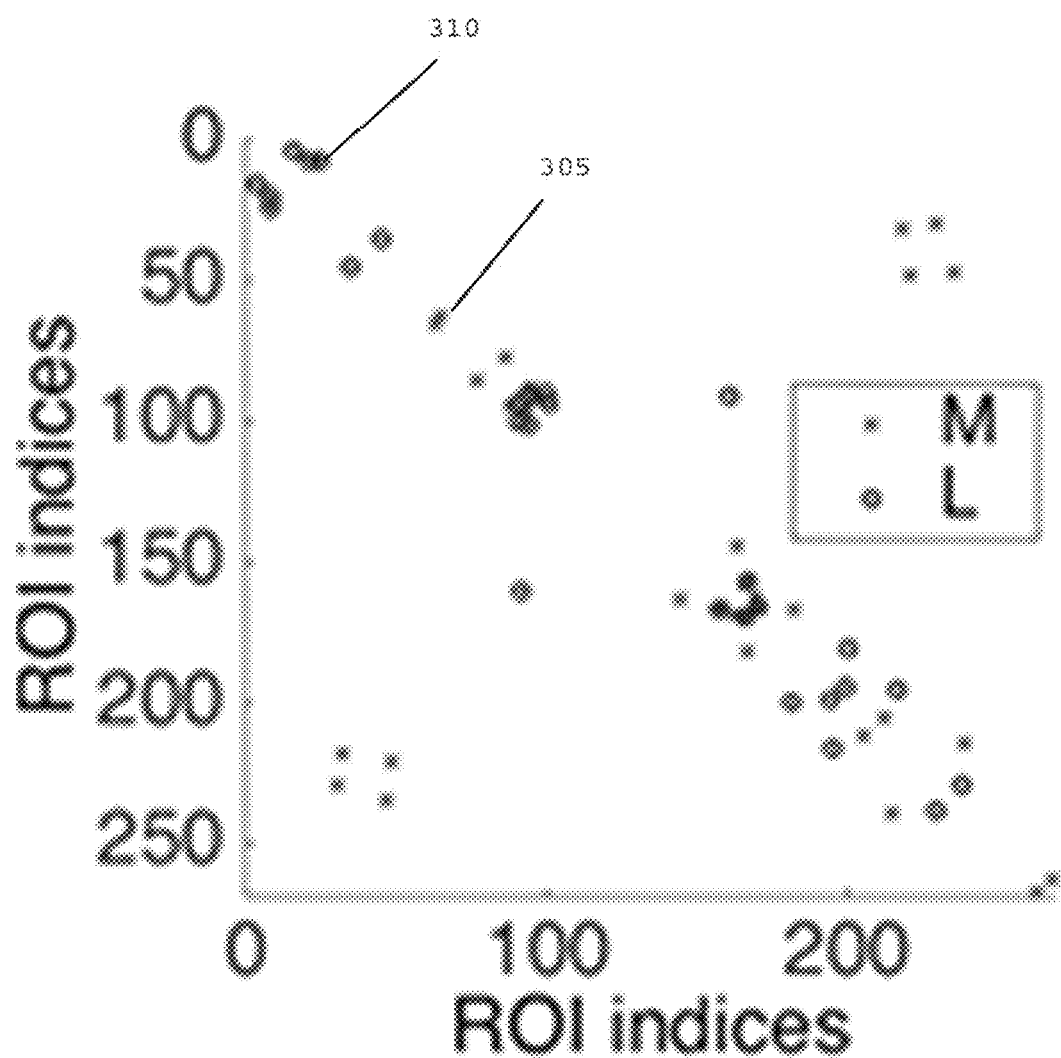
FIG. 3 is an exemplary chart illustrating region-of-interest couples with P<0.01 according to an exemplary embodiment of the present disclosure.
Figure 4:
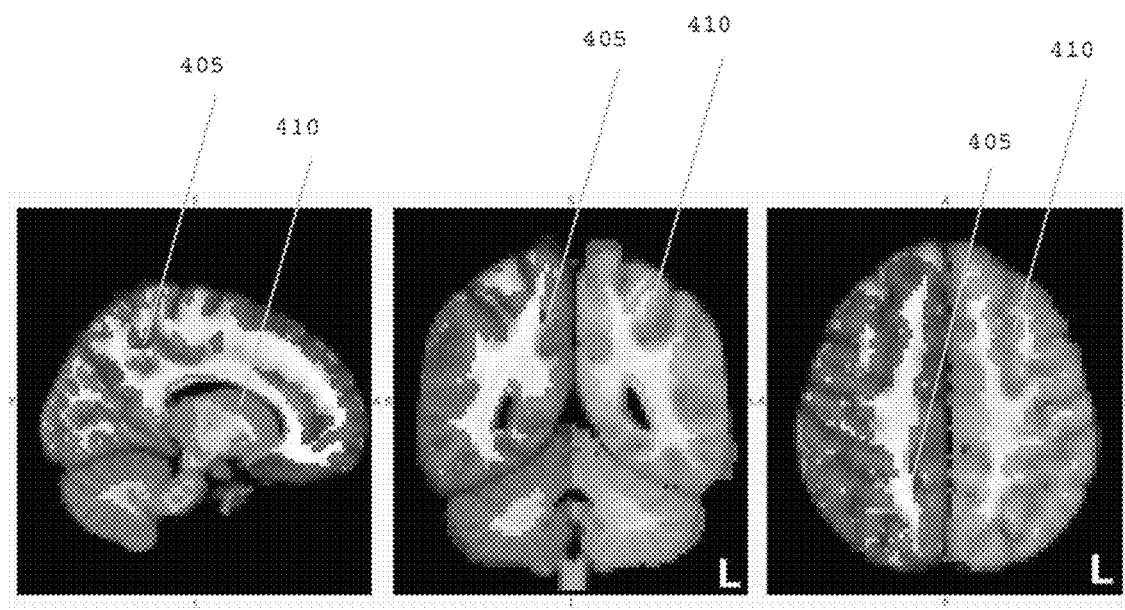
FIG. 4 is a set of exemplary images of traumatic brain injury-related clusters on an atlas according to an exemplary embodiment of the present disclosure.

The region of interest (ROI) couples showing significant group difference (e.g., p<0.01) on the original feature matrix M and the low rank matrix L (e.g., from FIG. 1) are shown in FIG. 3. Although there can be an overlap between the two sets of results, some ROI pairs detected on M (305) may no longer be found to be statistically significant in the analysis of L (310), especially the ones far from each other (e.g., located on the upper-right and lower-left corner of FIG. 3). These ROI connections can be more vulnerable to noise and outliers because of their corresponding fiber lengths. Further, other exemplary ROI pairs may only show group difference on L after the outlier components can be removed from features matrix M. Previous whole-brain analyses (see e.g., Reference 8) have found TBI-related changes near the Precuneus. This area (e.g., shown as element 405 in the exemplary images of FIG. 4) overlap with three ROIs (e.g., 44, 90, 91) from the atlas used in this exemplary study (e.g., shown as shaded resins 410). The minimum p values of most or all connectivity t-tests involving the three ROIs are listed in Table 1 below. The three exemplary ROIs showed smaller minimum p on L, indicating the enhancement of group difference after L+S decomposition. In particular, ROI 44 showed trending connectivity differences (e.g., p=0.0306) on the L matrix, but not on the M matrix.

TABLE 1

| Minimum p-values of connectivity t-tests on L and M | | | |
|---|---|---|---|
| Min P | ROI 44 | ROI 90 | ROI 91 |
| M | 0.5898 | 0.2820 | 0.1280 |
| L | 0.0306 | 0.1478 | 0.1094 |

Further Exemplary Methods

Radial DSI datasets of two crossing fiber bundles (e.g., 60°, (1.0/0.1)/0.1 μm 2/ms) and a water pool (e.g., 10%) were simulated with Radial (e.g., 59 radial lines, 4 shells) q-space sampling. (See, e.g., Reference 12). Rician noise (e.g., SNR 30 in b0) and group-outliers (e.g., 10%, SNR 5) were added to the simulated diffusion signals. Each group contained 100 ODFs, simulating a study with 100 co-registered cases per group. Group differences were simulated by changing the Axial $D_{ax}$ or Radial $D_{rad}$ diffusivity of one of the fibers or the crossing fiber angle.

Exemplary in Vivo Measurements

To determine the ODF group difference detection, DSI datasets of two subgroups of the "Steven and Alexandra Cohen Veterans Center for the Study of Post-Traumatic Stress and Traumatic Brain Injury"-study were used (e.g., 33 healthy controls (e.g., 26 male/7 female, 30±7 (e.g., 22-59) years old); 62 volunteers with Traumatic Brain Injury (e.g., TBI, 4.1±2.5 (1-12) TBIs, 1.4±0.8 (1-5) TBIs with loss of consciousness, 6.5±7.1 (1-40) years since last TBI with loss of consciousness, 59 male/3 female, 33±7 (21-51) years old). In vivo brain DSI datasets were acquired using a twice-refocused spin echo EPI sequence (e.g., 3 T Skyra, Siemens; 32-ch head coil; TR/TE=2600/114 ms, 52 slices, 2.2 mm isotropic, parallel imaging (e.g., 2×, GRAPPA) and simultaneous multi-slice acceleration of 4 (see, e.g., Reference 19), 10:49 min; max b=4000, Radial q-space sampling (e.g., 59 radial lines, 4 shells (see, e.g., Reference 12)). Post-processing was performed offline. Exemplary images were corrected for susceptibility, eddy currents and movement (e.g., eddy, FSL) and registered to the T1-weighted MNI152-atlas (e.g., elastix/transformix (see, e.g., Reference 20)). Radial Diffusion Spectrum Imaging reconstructions were performed (Matlab, Mathworks) and displayed. (See, e.g., Reference 21).

Exemplary Group Difference Test

Figure 5:
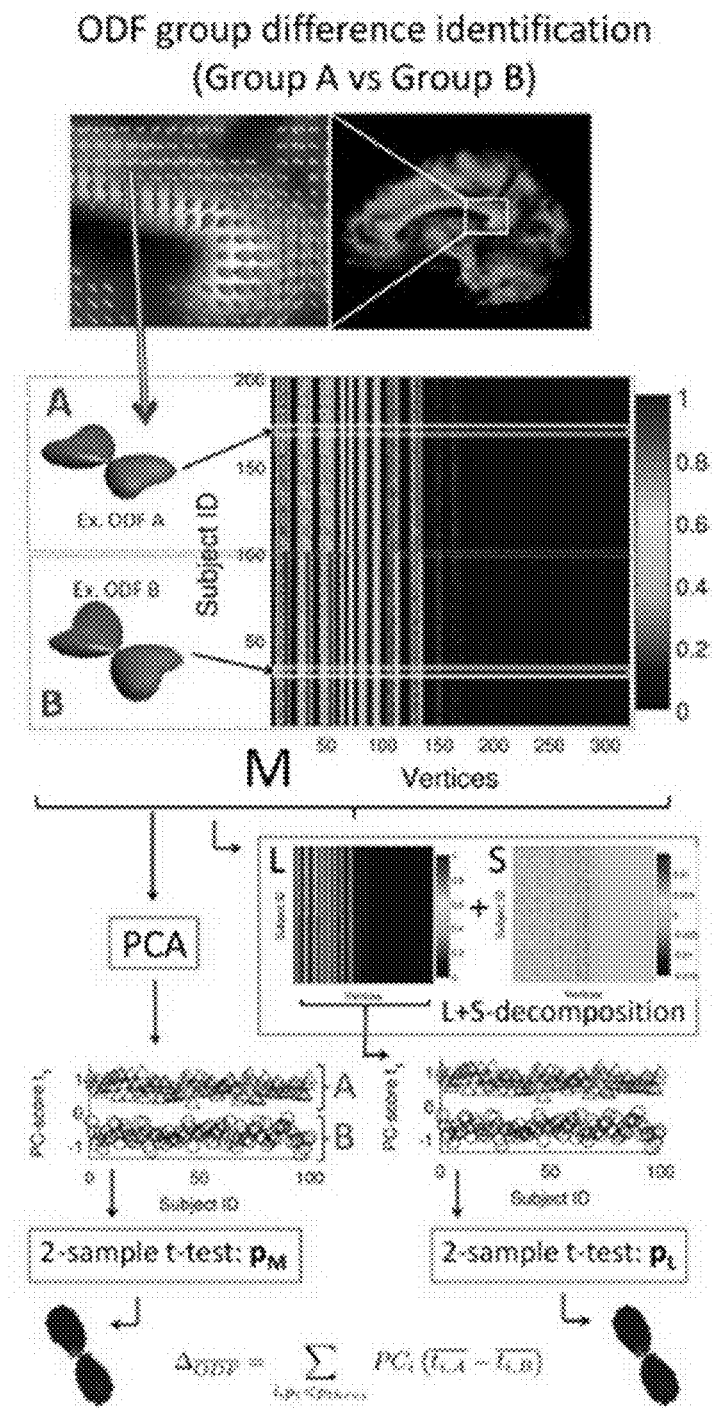
FIG. 5 is a set of exemplary diagrams illustrating the differences between two groups of Orientation Distribution Functions in a registered voxel identified by reorganizing Orientation Distribution Function-values according to an exemplary embodiment of the present disclosure.

To test for voxel-wise group differences, the ODF-values of both groups can be reorganized in a matrix M, 1 ODF per row, (see, e.g., diagrams shown in FIG. 5) and M can be decomposed as the sum of a Low-Rank matrix L and a Sparse Matrix S (M=L+S) (see, e.g., References 17 and 18), using an exemplary Alternating Directions procedure. This exemplary decomposition can estimate the underlying reduced noise ODFs by minimizing the rank of L, while separating the sparse noise and outliers in S. (See, e.g., FIG. 5). From the Singular Value Decomposition of L in the L+S decomposition, the PC can be derived. The PC-scores (e.g., the projections of the ODFs on the PC) of L can then be used to evaluate group differences (e.g., two sample t-test). The exemplary system, method and computer-accessible medium, according to an exemplary embodiment of the present disclosure, can utilize PCA performed on M (e.g., rather than on L) to generate PCs and PC-scores. (See, e.g., Reference 16).

Exemplary Results

Figures 6A, 6B, 6C:
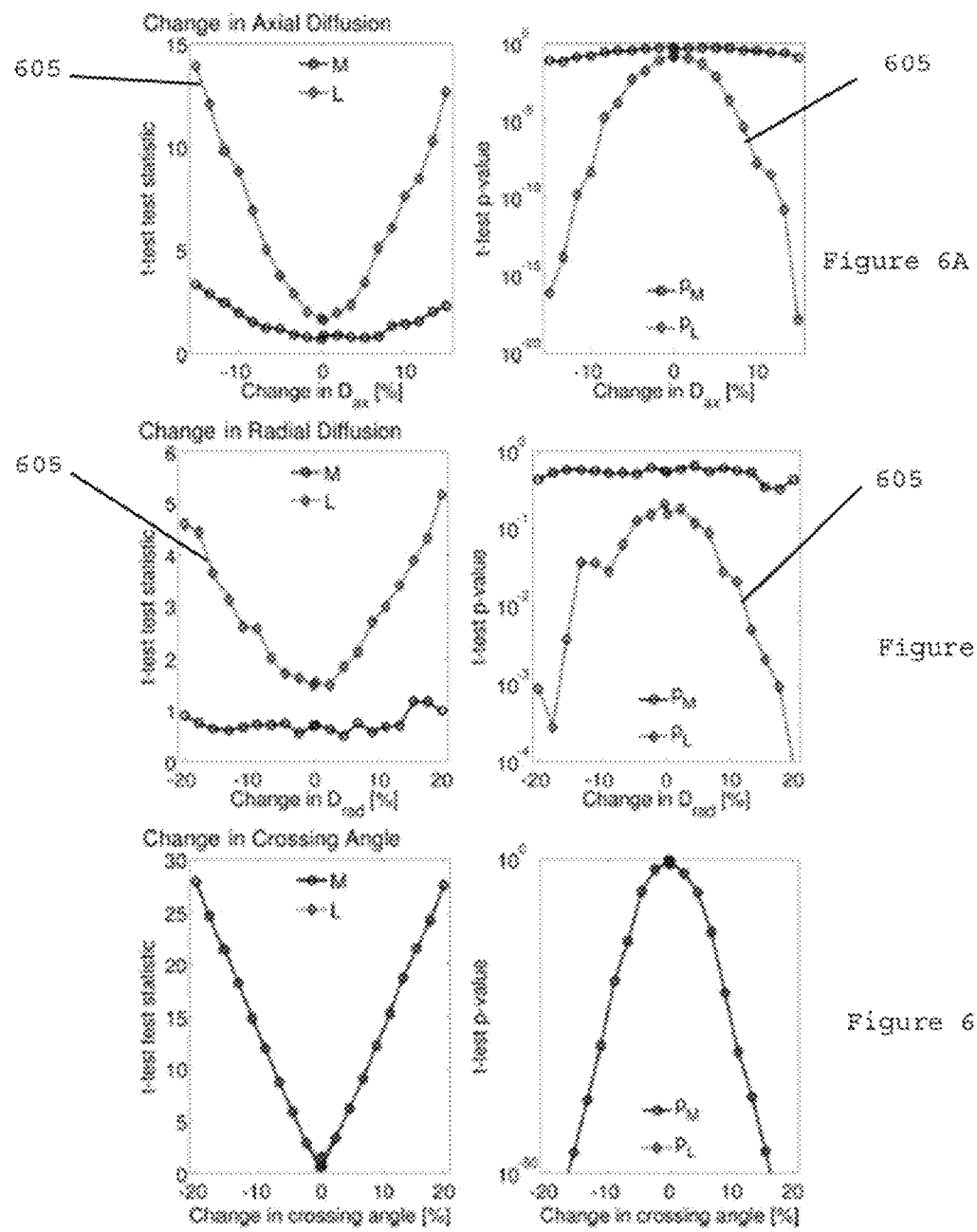
FIG. 6A is an exemplary set of graphs illustrating exemplary simulations of percent changes in Axial Diffusion according to an exemplary embodiment of the present disclosure.
FIG. 6B is an exemplary set of graphs illustrating exemplary simulations of percent changes in Radial Diffusion according to an exemplary embodiment of the present disclosure.
FIG. 6C is an exemplary set of graphs illustrating exemplary simulations of percent changes in crossing angle of Orientation Distribution Functions according to an exemplary embodiment of the present disclosure.
Figure 7:
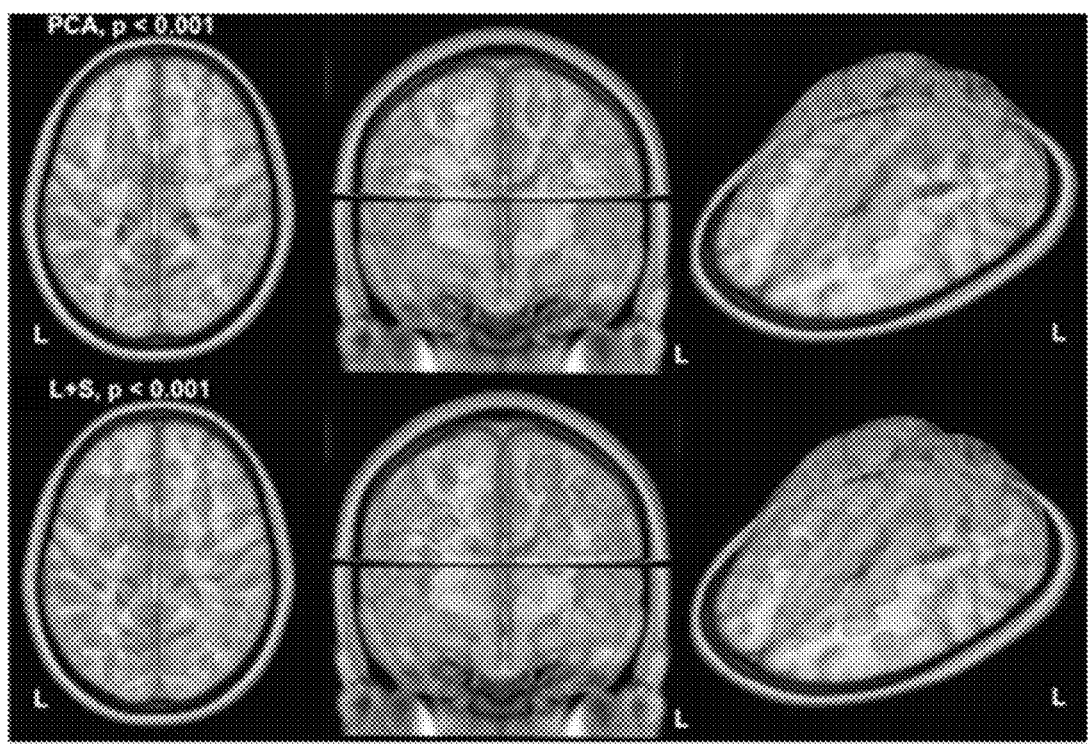
FIG. 7 is a set of exemplary images illustrating group differences detected between controls and veterans who suffered from traumatic brain injuries according to an exemplary embodiment of the present disclosure.

Simulations of graph shown in ODF group comparisons (e.g., FIGS. 6A and 6B) illustrate that the differences in $D_{ax}$ (see, e.g., FIG. 6A) and $D_{rad}$ (see, e.g., graph shown in FIG. 6B) can be detected with increased significance when using the L+S-decomposition rather than the PCA-analysis. Separating noise and outliers in S can improve the detection of ODF group differences in L. Changes in crossing angle (see, e.g., graph shown in FIG. 6C) can be detected equally well by both approaches as these can correspond to a shift in the ODF-peak positions rather than a more subtle change in the ODF-peak amplitudes. The improved group difference detection can be reflected in the in vivo dataset (see, e.g., images shown in FIG. 7) which shows that more regions can be identified as significantly different with the L+S-based statistical test.

The exemplary system, method and computer-accessible medium, according to an exemplary embodiment of the present disclosure, can isolate the ODF features in each voxel that can be common or different within or between, subject cohorts from the individual subject variability. This can be achieved, for example, by replacing the PCA by a Low-Rank plus Sparse ("L+S") Matrix Decomposition (see, e.g., References 58-60) of the ODF distributions. The L+S decomposition also referred to as Robust PCA ("RPCA"), can separate the sparse individual variability in the sparse matrix S while recovering the essential ODF features in the low-rank matrix L. Subsequently, statistical tests can focus on the defining ODF features in L, increasing the detectability of group differences in the diffusion datasets. This can then be extended to a whole brain analysis using TFCE. (See, e.g., Reference 51). Although this can be applied to the diffusion ODF, as derived from Q-Ball imaging (see, e.g., Reference 28), DSI (see, e.g., Reference 22), Generalized Q-Space Sampling ("GQI") (see, e.g., Reference 61), it can also be applicable to the fiber ODF ("fODF") obtained by spherical deconvolution. (See, e.g., Reference 62).

The L+S matrix decomposition can be used by the exemplary system, method and computer-accessible medium for the isolation of the low-rank defining ODF features. It can be used to recover both the low-rank and the sparse components exactly under limited restrictions of rank and sparsity. (See, e.g., References 58 and 59). In addition, it can be used for tasks such as image alignment (see, e.g., Reference 63), denoising and background extraction in video (see, e.g., References 57 and 64), segmentation of images and video (see, e.g., References 57 and 64), reconstruction of diffusion MRI (see, e.g. Reference 65), dynamic CT (see, e.g., Reference 66) and MRI (see, e.g., Reference 60) images, and filtering of fMRI datasets. (See, e.g., Reference 67).

The ODF features identified in L in each voxel, the Principal Components of L, can be ODFs forming a basis for the ODFs of all group members in that voxel. While group differences can be identified based on the significant differences between PC-scores of groups, this basis of ODFs can be used to calculate group difference ODFs $\Delta_{ODF}$. This $\Delta_{ODF}$ can be composed of ODF features which can be different between groups weighted by the difference in PC-scores. They can be used for visualization of the differences between subject groups, or as a basis for tractography, similar to a local tractography visualization approach. (See, e.g., Reference 49).

The ODFs in each voxel of a set of registered whole brain diffusion datasets can be expected to be highly correlated within that voxel. (See e.g., diagrams shown in FIG. 5). Although subject subgroup differences can arise, all ODFs can be assumed to be drawn from a lower-dimensional subspace. This means that the ODF features which can be common between or within subject groups can be captured in that low-dimensional subspace, and the spare individual variability can be ignored. The low-dimension assumption of the ODFs can be translated in an assumption of low rank. (See, e.g., References 56 and 57). The rank of a matrix can be the dimension of the basis needed to represent all entries in that matrix. Thus, when the low-rank subspace of the ODFs can be identified, the ODF features that are different between subject subgroups can be identified.

The exact recovery of both the low-rank and sparse components of matrices (see, e.g., References 58 and 59) has been of great interest in a number of applications. (See, e.g., References 57, 60 and 63-67). Separating these components facilitates focus on either the common features, or the dynamic aspects of datasets, respectively, the low-rank L and sparse S submatrices. The L+S matrix decomposition, also referred to as Robust PCA, can be commonly expressed as, for example:

$$\text{minimize } \|L\|_* + \lambda \|S\|_1 \tag{1}$$

$$\text{subject to } L+S=M \tag{2}$$

with M the matrix to decompose, $\|.\|_*$, the nuclear norm defined by the sum of all singular values as a surrogate for low-rank (see, e.g., Reference 68), $\|.\|_1$ the $l_1$-norm defined by the element-wise sum of all absolute values as a surrogate for sparsity (see, e.g., Reference 68) and $\lambda$ a trade-off between the sparse and low-rank components to be recovered. Recent advances have shown that both components L and S can be recovered exactly from Munder limitations of sparsity and rank. (See, e.g., References 58, 59 and 68). In addition, recoverability can be independent of the magnitude of outliers, as it can depend on the sparsity of the outliers. (See, e.g., Reference 57). It has also been shown that the problem in Eq. 1 can be solved computationally efficient with the alternating directions method ("ADM") (see, e.g., Reference 68), a method based on augmented Lagrange Multipliers. (See, e.g., Reference 69).

The L+S-decomposition can be used to identify the low-rank subspace of ODFs in a matrix of vectorized ODFs of a single voxel of a set of registered brains. (See e.g., diagrams shown in FIG. 5). It can be used to recover the sparse individual variability in S, (see e.g., FIG. 5); facilitating the subsequent statistical tests to focus on the key ODF features in the subject groups captured in the low-rank basis of L. Of this low-rank basis, the PC scores can be used as input for statistical testing.

Figure 8:
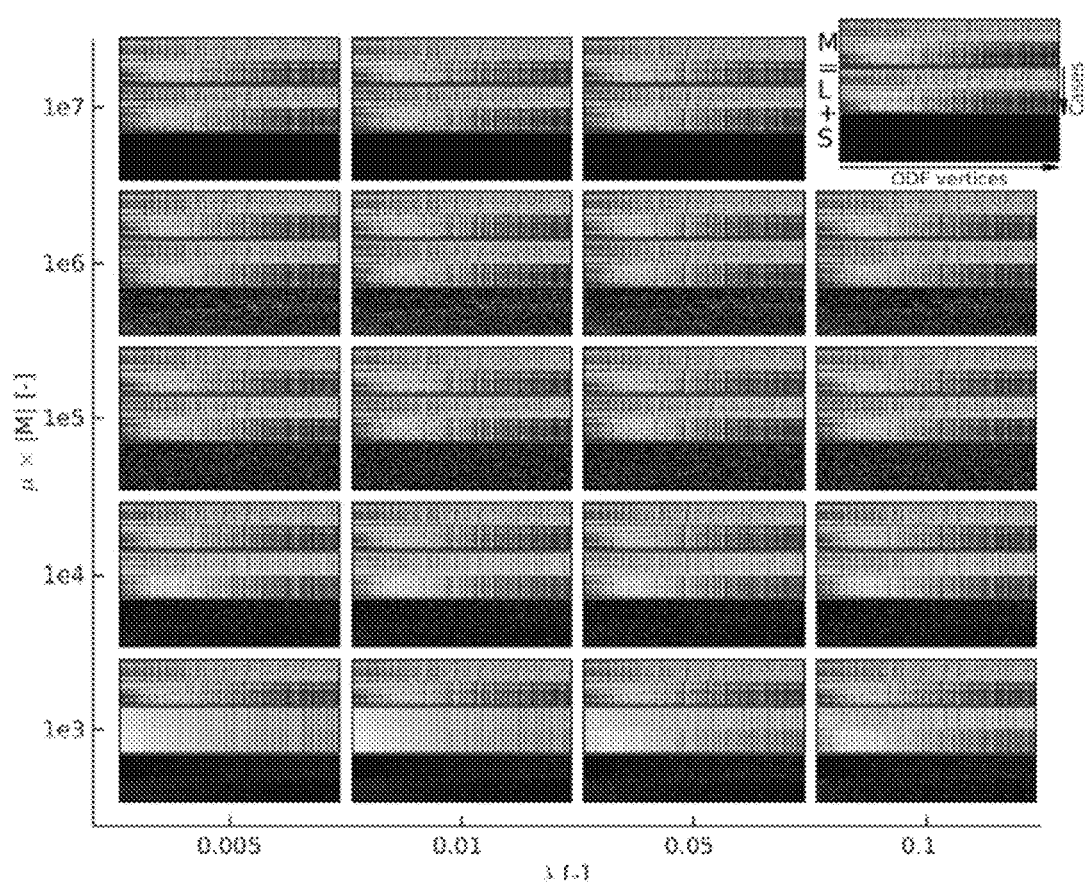
FIG. 8 is a set of exemplary images illustrating the impact of a regularization parameter according to an exemplary embodiment of the present disclosure.

The L+S-matrix decomposition solved using the exemplary ADM-method can have two tunable parameters $\lambda$ (see e.g., Eq. 1) and $\mu$, an ADM penalty parameter. The parameter $\lambda$ can balance L and S in Eq. 1; a higher $\lambda$ can put more emphasis on the sparsity of S while a lower $\lambda$ can force the rank of L down. Although the outcome of Eq. 1 can depend on the choice of $\lambda$, it was shown mathematically that a whole range of values of $\lambda$ can ensure the exact recovery of L and S from Eq. 1. (See, e.g., Reference 58). A universal choice of $\lambda=1/\text{sqrt}(n)$ with $n=\max(n_1, n_2)$ and $n_1, n_2$ the dimensions of M has been suggested (see, e.g., References 58 and 69) and successfully applied in a large number of applications. $\lambda=1/\sqrt{n}\sim 0.06$ can be used when observing 321 vertices per ODF and ±100 subjects, though a wide range of $\lambda$ performs as expected. (See e.g., images shown in FIG. 8).

The variable $\mu$ can be the penalty parameter in the ADM search procedure for the violation of the linear constraint $\|L+S-M\|$ which can be facilitated during the search. A large $\mu$ can enforce a very sparse S while a small $\mu$ can decrease the rank of L. Thus, it can be beneficial to select an appropriate value of $\mu$. $\mu=\frac{1}{4}n_1n_2/\|M\|$, a value also used elsewhere, has been proposed. (See, e.g., References 58 and 68). Here, $\mu=25n_1n_2/\|M\|$, a value about 100 times larger, can be used. Calculations (see e.g., images shown in FIG. 8) show that this value $\mu\times\|M\|25n_1n_2\sim610^5$ can balance the sparsity of S with the low-rankness of L.

The L and S components of M can be recovered with a high probability when L can be sufficiently low rank, and S sufficiently sparse (see, e.g., References 56, 58, 59 and 68). The limit for the average normalized rank $\text{rank}(L)/\min(n_1, n_2)$ of the L matrices was previously identified (see, e.g., Reference 58) as $\text{rank}(L)/\min(n_1, n_2) \leq c_1/\log(n)^2 \sim c_1 0.03$ with $c_1$ an positive constant was identified. Similarly, the upper limit for the normalized cardinality $m/(n_1, n_2)$, counting the non-zero elements of a matrix as a measure for sparsity, $m(S)/(n_1, n_2) \leq c_2$ with $c_2$ a positive constant. (See, e.g., Reference 58). While the constants $c_1$ and $c_2$ may not be known, simulation results (see, e.g., References 58 and 68) indicate that the recovery of L and S can be valid for normalized rank values below about 0.1 and normalized cardinalities below about 0.2. The normalized rank and cardinality values averaged over the whole brain for L and S matrices recovered from single voxel matrices of vectorized ODFs can be about 0.07±0.02 and about 0.17±0.07 respectively. Thus, the low-rank subspace of ODFs in a matrix of vectorized ODFs of a single voxel can be reliably identified using the exemplary L+S-decomposition.

When the low-rank subspace of ODFs can be identified in each voxel of registered whole brain diffusion data sets, the PC-scores in these low-rank bases can be used as input for statistical testing. (See, e.g., FIG. 5). The large numbers of multiple comparisons in these tests can be corrected using the exemplary TFCE method (see, e.g., Reference 51), which can obviate the need for a suitable cluster threshold choice. (See, e.g., Reference 70). In addition, combining TFCE permutation inference with complex General Linear Models ("GLM") can facilitate accounting for nuisance variables. (See, Id.). These methods can assume that the joint probability distribution of the variables does not change if they are rearranged. (See, Id.). This can be a valid assumption since the joint distribution of errors of the ODFs PC-scores can be assumed to be invariant on exchange. (See, e.g., Reference 71). Significance of group differences can be assessed based on the p-values fully corrected for multiple comparisons across space (see, e.g., Reference 51) calculated from the TFCE-output.

Figures 10A, 10B, 10C:
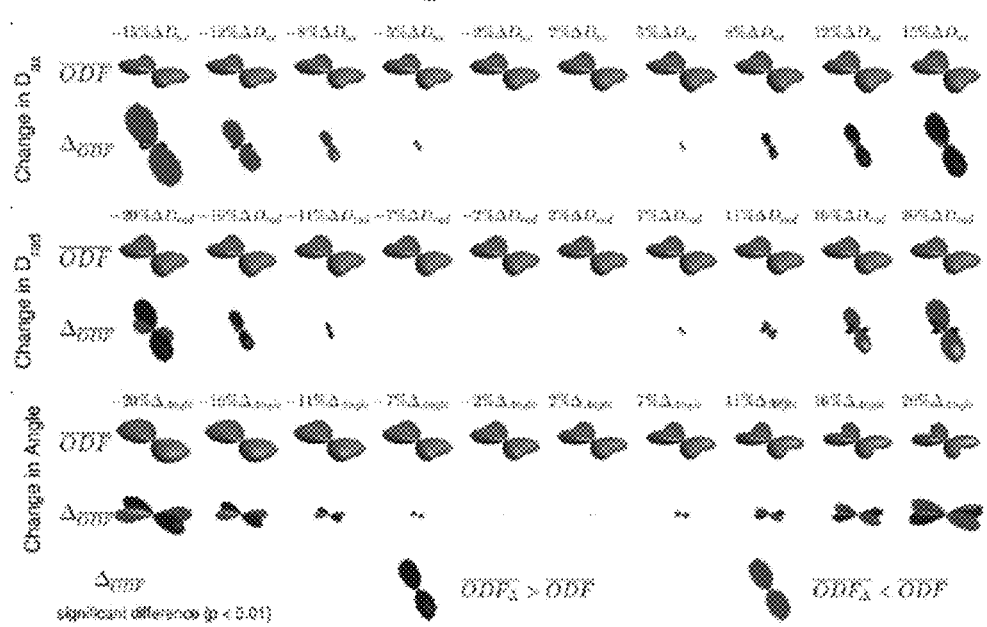
FIGS. 10A-10C are exemplary diagrams illustrating difference Orientation Distribution Functions of exemplary simulations of two groups of two crossing fibers according to an exemplary embodiment of the present disclosure.

In addition to group difference significance, the low-rank basis of the ODFs in each voxel can be used to calculate difference ODFs $\Delta_{ODF}$ between subject groups A and B ($n_A, n_B$ members) based on the Principal Components ($PC_i$) and their PC-scores ($t_{i,j}$), where, for example:

$$\Delta_{ODF} = \sum_{i, p_i < p_{thres}} PC_i \left( \frac{1}{n_A} \sum_{j \in A} t_{i,j} - \frac{1}{n_B} \sum_{j \in B} t_{i,j} \right) \quad (3)$$

which can applied for the PCs which were detected to hold significant differences $p_i < p_{thres}$ between groups. Similarly, when observing trends related to a demographic variable, the correlation ODF $R_{ODF}$ can be calculated as, for example:

$$R_{ODF} = \sum_{i, p_i < p_{thres}} PC_i r_i \quad (4)$$

where $r_i$ can be the correlation coefficient between $t_{i,j}$ and the demographic variable. The ODFs in Eqs. 3 and 4, obtained from statistical analysis, can be expressed in the same physical quantities as the original ODFs since they can be expressed in terms of PC-basis. They can be used for visualization of the significant differences between subject groups. (See e.g., diagrams shown in FIGS. 10A-10C), significant trends in the dataset or as a basis for tractography visualization. The latter approach can be similar to the local tractography approach. (See, e.g., Reference 49).

The difference ODFs $\Delta_{ODF}$ can illustrate the effect of differences in the underlying diffusion properties of the fiber bundle in the voxel. Since the spatial extent of each peak can be related to the Quantitative Anisotropy ("QA") (see, e.g., Reference 61), both increases in $D_{ax}$ and decreases in $D_{rad}$ can increase the peak length. (See e.g., diagrams shown in FIGS. 10A-10C). Similarly, both decreases in $D_{ax}$ and increases in $D_{rad}$ can decrease the peak length. Thus, in the difference ODFs, both possible changes can be encapsulated, possibly missing compensating changes.

Exemplary Simulated ODF Generation

Single voxel groups of RDSI datasets of two or more crossing fiber bundles with equal weight (e.g., 60, $\lambda_1/\lambda_2/\lambda_3$ 1.00/0.10/0.10 $\mu m^2$/ms) and a water pool (e.g., 10%) were simulated with Radial q-space sampling (e.g., 59 radial lines, 4 shells, $b_{max}=4000$ s/mm$^2$, (see, e.g., Reference 37)). Rician noise (e.g., SNR 30 in non-diffusion-attenuated signal) and group-outliers (e.g., 10%, SNR 5%) were added to the simulated diffusion signals before reconstructing the ODFs. (See, e.g., Reference 28). Each single voxel group contained about 100 ODFs, simulating a study with about 100 co-registered cases per group. The group differences were emulated by changing Axial diffusivity ($D_{ax}=\lambda_1$), Radial diffusivity ($D_{rad}=(\lambda_2+\lambda_3)/2$) of one of the two fibers fiber or crossing fiber angle of one group. Since these were single-voxel simulations, two-sided Student's t-test (e.g., 5% significance level) test statistics and p-values were used to evaluate the detectability of simulated group differences. To improve the clarity of display, the average ODFs of each group were plotted where appropriate.

Exemplary in Vivo Acquisitions

In vivo subject datasets were taken from two large ongoing neuro-imaging experiments. The first dataset, was taken from subgroups (see e.g., Table 2 below) of a veterans study. The selection of a group of healthy controls and a group who suffered TBI with Loss of Consciousness ("LOC") in this veteran population can facilitate group to group comparisons. These datasets where collected on a Siemens 3 T Skyra system (e.g., Siemens Erlange) using a 20-Ch head coil. For every subject, a whole brain Radial DSI scan was performed using a Twice Refocused Spin Echo sequence ("TRSE") radial q-space sampling on 59 radial lines, with 4 shells, 236 total q-space samples, $b_{max}=4000$ s/mm$^2$; TR/TE=2600/114 ms, 2.2 mm isotropic resolution, 220 mm Field of View, 60 slices, parallel imaging (e.g., 2×, GRAPPA) and simultaneous multi-slice acceleration of 4 (see, e.g., Reference 34); acquisition time of 10:49 min). In addition, a $T_1$ weighted rapid gradient-echo sequence (e.g., MPRAGE) was acquired as a Reference for image registration (e.g., TR/TE=2300/2.98 ms, 192 slices, 1×1×1 mm resolution, TI=900/1000 ms, parallel imaging (e.g., 2×, GRAPPA), 5:03 min) and a double-echo gradient echo sequence (e.g., TR/TE=843/8 ms, 2.2 mm isotropic resolution) for field map calculation.

A second dataset, referred to below as HCP, was used. 355 subjects were selected. Diffusion imaging using mono-polar gradient pulse sequence (e.g., 6 $b_0$-images and 270 q-space samples on three shells, b=1000,2000 and 3000 s/mm$^2$; all diffusion directions were acquired twice, one with phase encoding left-to-right and once with phase encoding right-to-left; TR/TE=5500/89.50 ms, 1.25 mm isotropic resolution, 210×180 mm Field of View, 111 slices, simultaneous multi-slice acceleration of 3 Reference; acquisition time of approximately 55 min) and structural imaging (e.g., MPRAGE; TR/TE=2400/2.14 ms, 192 slices, 1×1×1 mm resolution, TI=900/1000 ms, parallel imaging (e.g., 2×, GRAPPA), 5:03 min) was performed on a Siemens 3 T Skyra with 100 mT/m maximum gradients.

Exemplary Data Preprocessing

The simulation results (e.g., 10000 ODF's for each parameter combination) were compared using the normalized root-mean-square-error ("NRMSE") and Jensen-Shannon Divergence ("JSD") (see, e.g., Reference 72) of the ODF's relative to the mean ODF of the highest b-value simulation.

ODF group comparisons (See e.g., FIGS. 9A-9F), where one group has reduced $D_{rad}$ show that statistical tests of the PC-scores for the ODF-matrix M ($p_M$) and the Low-Rank matrix L($p_L$) can detect large differences (e.g., 50%) in $D_{rad}$. A similar analysis demonstrates that smaller differences, in the range of about 10% to about 20%, in $D_{rad}$ can be more robustly identified through the PCA analysis of L than that of M. Thus, by separating noise and outliers in S, the PCA analysis of L can improve the detection of ODF group differences. This can improve the detection of differences in both $D_{ax}$ and $D_{rad}$. (See e.g., graphs shown in FIGS. 6A and 6B). Changes in crossing angle (see e.g., graph shown in FIG. 6C) can be detected equally well by both approaches as these can correspond to a shift in the peaks of the ODF rather than a change in their heights. There can be a linear relationship between test statistics and changes in diffusion parameters (See e.g., graphs shown in FIGS. 6A-6C).

The difference ODFs display the significant deviations between ODF groups (see e.g., graphs shown in FIGS. 6A-6C), aiding in visual interpretation of the results. These difference ODFs can potentially be used as input for tractography procedures.

TABLE 2

Demographic data of subjects (TBI: Traumatic Brain Injury; LOC: Loss of Consciousness)

|  | Control | TBI |
| --- | --- | --- |
| Cases | 26 (male) | 52 (male) |
| Age yr | 29 ± 5 (22-43) | 30 ± 5 (21-44) |
| # TBIs | 2.1 ± 1.6 (0-6) | 4.2 ± 2.6 (1-12) |
| # TBIs with LOC | 0 ± 0 (0-0) | 1.4 ± 0.8 (1-8) |
| Time since last TBI with LOC yr | 0 ± 0 (0-0) | 7.7 ± 8.4 (1-37) |

L+S matrix decomposition of ODF distributions can provide a foundation for improved detection of group differences in DSI via PCA-analysis. Significant group differences can be visualized with difference ODFs. The exemplary system, method and computer-accessible medium, according to an exemplary embodiment of the present disclosure, method can aid in the detection of smaller group differences in clinically relevant settings as well as in neuroscience applications.

FIG. 11A shows an exemplary diagram illustrating an evaluation of Orientation Distribution Function group difference detection on groups of registered in vivo Orientation Distribution Functions according to an exemplary embodiment of the present disclosure. FIG. 11B shows an exemplary diagram illustrating an evaluation of Orientation Distribution Functions group differences taken from a segment of a brain according to an exemplary embodiment of the present disclosure. FIG. 11C illustrates an exemplary matrix of reorganized Orientation Distribution Functions according to an exemplary embodiment of the present disclosure. FIG. 11D is a set of exemplary charts illustrating the Jensen-Shannon Divergence according to an exemplary embodiment of the present disclosure. FIG. 11E shows a set of exemplary graphs illustrating the impact of the choice of the parameters λ and μ of the L+S-decomposition on the detection of significant Orientation Distribution Functions group differences according to an exemplary embodiment of the present disclosure.

As shown in FIGS. 11A-11E, the ODFs can be reorganized, and for all possible voxel combinations (see e.g., columns in the matrix shown in FIG. 11C), the JSD is plotted versus (i) the t-test p-value and (ii) t-statistic of M (e.g., PCA-analysis) and (iii) the p-value and (iv) t-statistic of L (e.g., L+S-analysis). (See e.g., graphs shown in FIG. 11D).

Figures 12A, 12B:
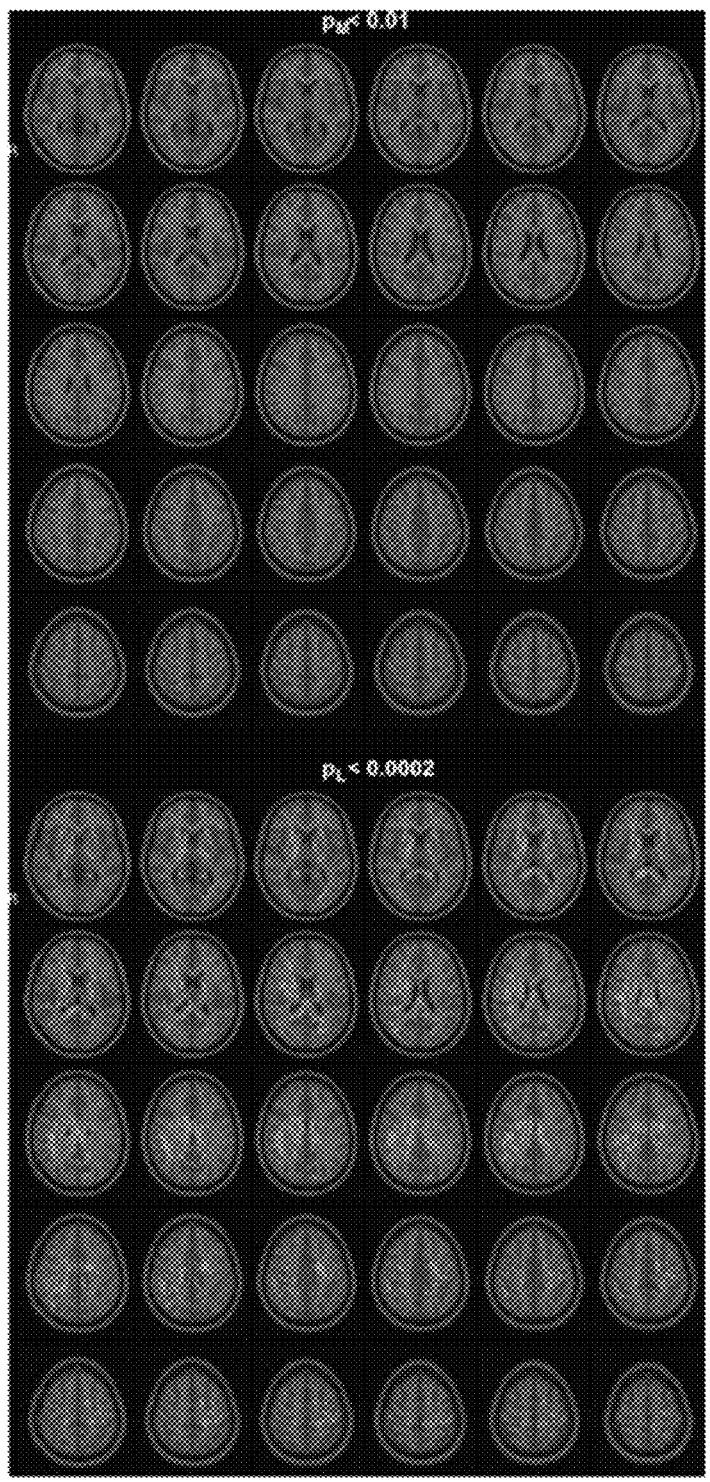
FIG. 12A is a set of exemplary images illustrating the detection of significant Orientation Distribution Function group differences between a healthy control and patients who suffer from a traumatic brain injury by analyzing the M-matrix according to an exemplary embodiment of the present disclosure.
FIG. 12B is a set of exemplary images illustrating the detection of significant Orientation Distribution Function group differences between a healthy control and patients who suffer from a traumatic brain injury by analyzing the L-matrix according to an exemplary embodiment of the present disclosure.

FIG. 12A illustrates a set of exemplary images illustrating the detection of significant Orientation Distribution Function group differences between a healthy control and patients who suffer from a traumatic brain injury by analyzing the M-matrix according to an exemplary embodiment of the present disclosure. (See e.g., Table 2). FIG. 12B shows a set of exemplary images illustrating the detection of significant Orientation Distribution Function group differences between a healthy control and patients who suffer from a traumatic brain injury by analyzing the L-matrix according to an exemplary embodiment of the present disclosure. Areas detected analyzing the M-matrix PCA-analysis (see e.g., FIG. 12A) and the low rank L-matrix (L+S-analysis) (see e.g., FIG. 12B) can be overlaid on the MNI-atlas.

Figures 13A, 13B:
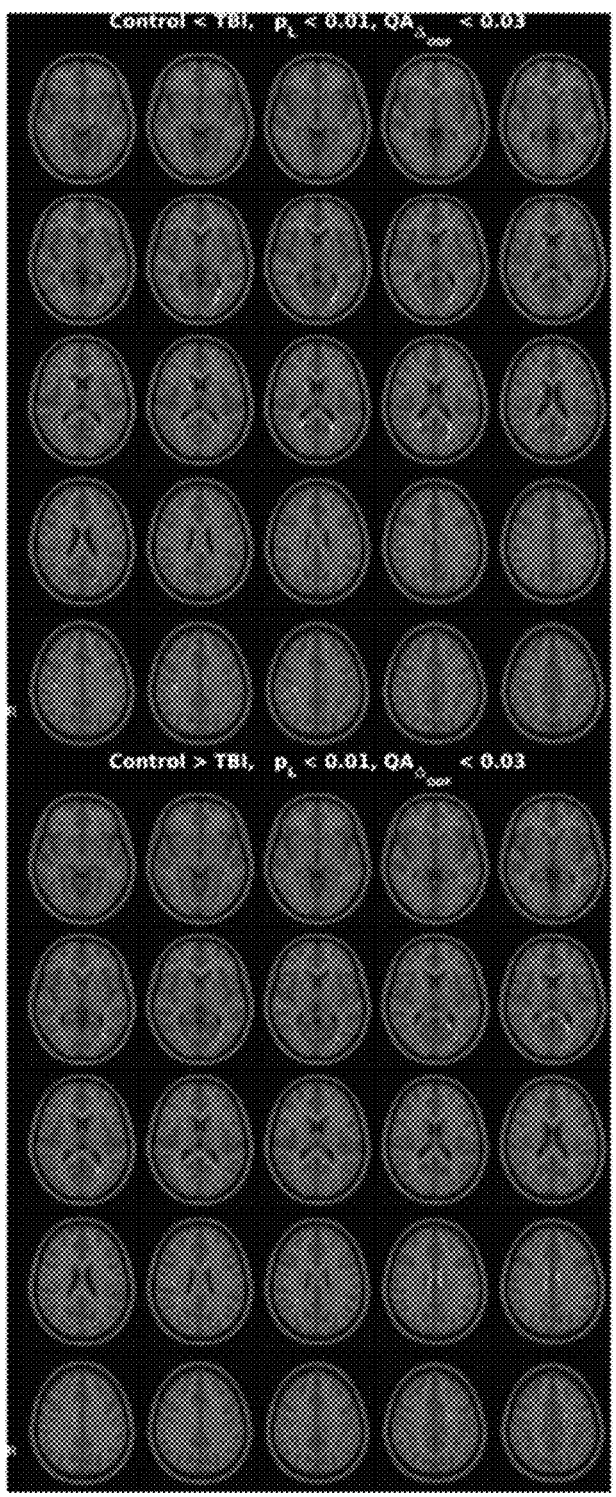
FIGS. 13A and 13B are set of exemplary images illustrating fiber directions identified from difference Orientation Distribution Functions as compared to healthy controls according to an exemplary embodiment of the present disclosure.

FIGS. 13A and 13B illustrate set of exemplary images illustrating fiber directions identified from difference Orientation Distribution Functions as compared to healthy controls according to an exemplary embodiment of the present disclosure. Fiber directions ($QA_{\Delta_{\overline{ODF}}}<0.03$) identified from the difference ODFs $\Delta_{\overline{ODF}}$(PL<0.01) calculated in the comparison between heathy control ("HC") and volunteers who suffered TBI (see e.g., Table 2), where $\Delta_{\overline{ODF}}$ with (a) $\bar{t}_{i,HC}<\bar{t}_{i,TBI}<$, (b) $\bar{t}_{i,HC}>\bar{t}_{i,TBI}$.

Figure 14A:
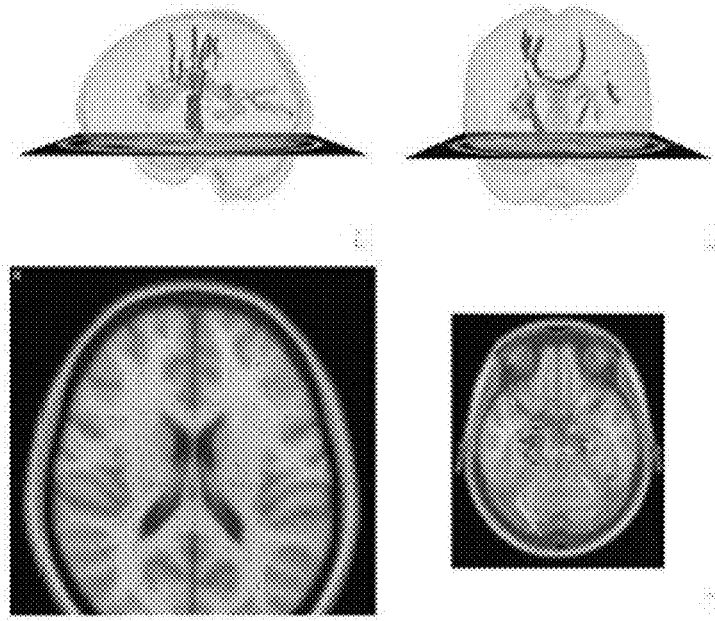
FIGS. 14A and 14B are further exemplary images illustrating the fiber tractography of the difference Orientation Distribution Functions as compared to healthy controls according to an exemplary embodiment of the present disclosure.
Figure 14B:
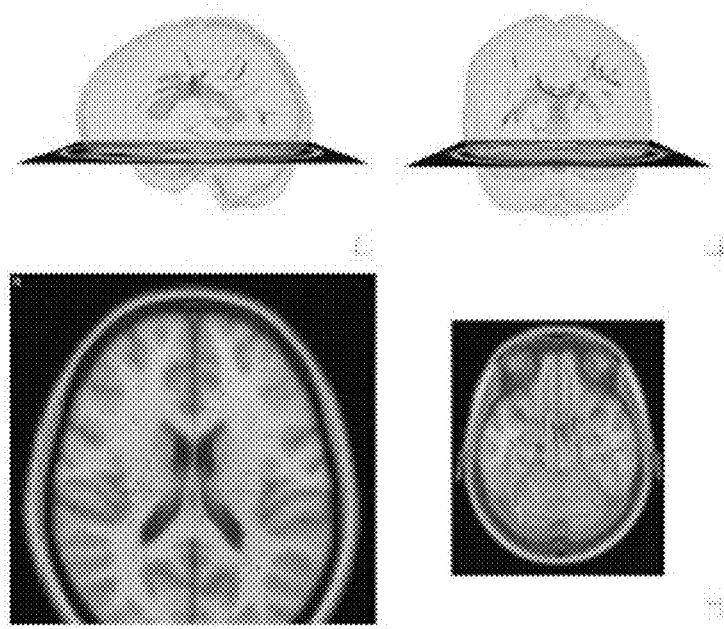

FIGS. 14A and 14B illustrate further exemplary images illustrating the fiber tractography of the difference Orientation Distribution Functions as compared to healthy controls according to an exemplary embodiment of the present disclosure. Fiber tractography of the difference ODFs $\Delta_{\overline{ODF}}$(PL<0.01) $QA\Delta_{\overline{ODF}}<0.03$) calculated in the comparison between HC and volunteers who suffer TBI (See e.g., Table 2).

Exemplary Conclusions

The exemplary system, method and computer-accessible medium, according to an exemplary embodiment of the present disclosure, can facilitate an accurate network modeling of structural connectivity. By "denoising" the connectivity features with the L+S decomposition, the robustness of detected group differences between the TBI and healthy control groups was improved. This provided robust TBI biomarkers from DSI data. The exemplary system, method and computer-accessible medium, can be extended to other anatomical atlases for connectivity, determining the relation between functional and structural networks, and cross-validation of the TBI-related features.

Figure 15:
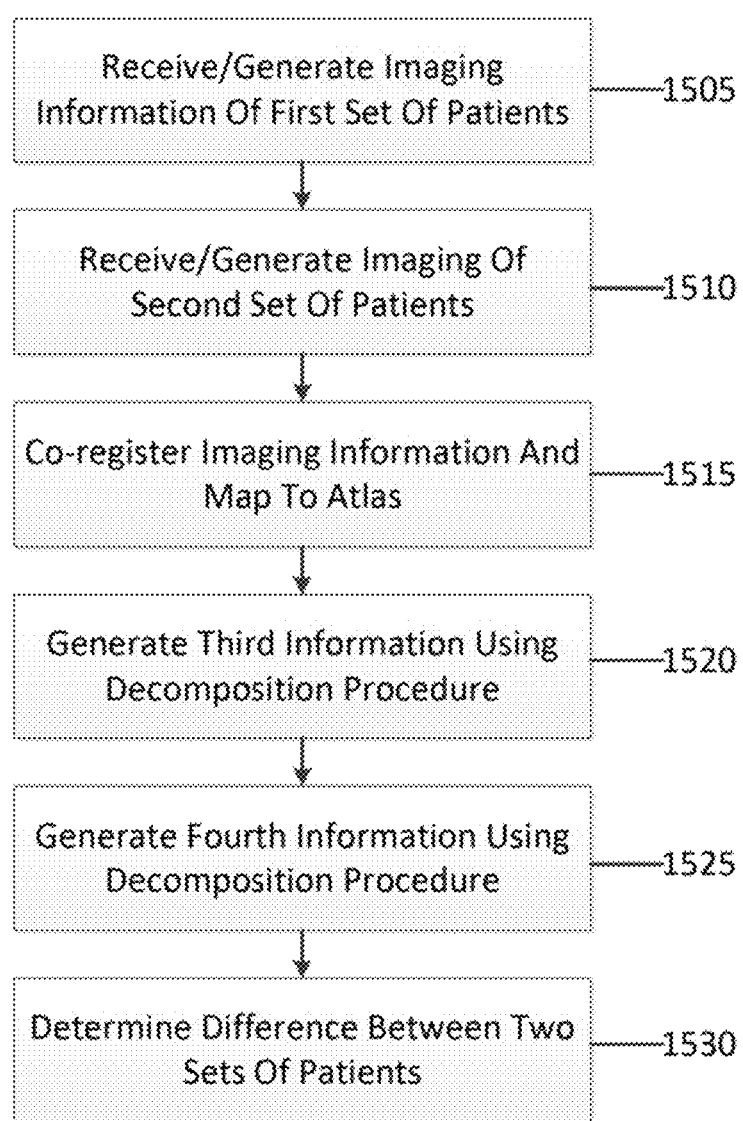
FIG. 15 is an exemplary flow diagram of an exemplary method for determining a difference(s) between two sets of patients according to an exemplary embodiment of the present disclosure.

FIG. 15 shows an exemplary flow diagram of an exemplary method 1500 for determining a difference(s) between two sets of patients according to an exemplary embodiment of the present disclosure. For example, at procedure 1505, imaging information of a first set of patients can be generated and/or received. At procedure 1510, imaging information of a second set of patients can be generated and/or received. At procedure 1515, the first and second imaging information can be co-registered and mapped to an atlas. At procedure 1520, third information (e.g., a matrix) can be generated using a first decomposition procedure, and at procedure 1525, fourth information (e.g., a matrix) can be generated using a second decomposition procedure. At procedure 1530, the difference between the first and second sets of patients can be determined based on the third and fourth information (e.g., based on the matrices).

Figure 16:
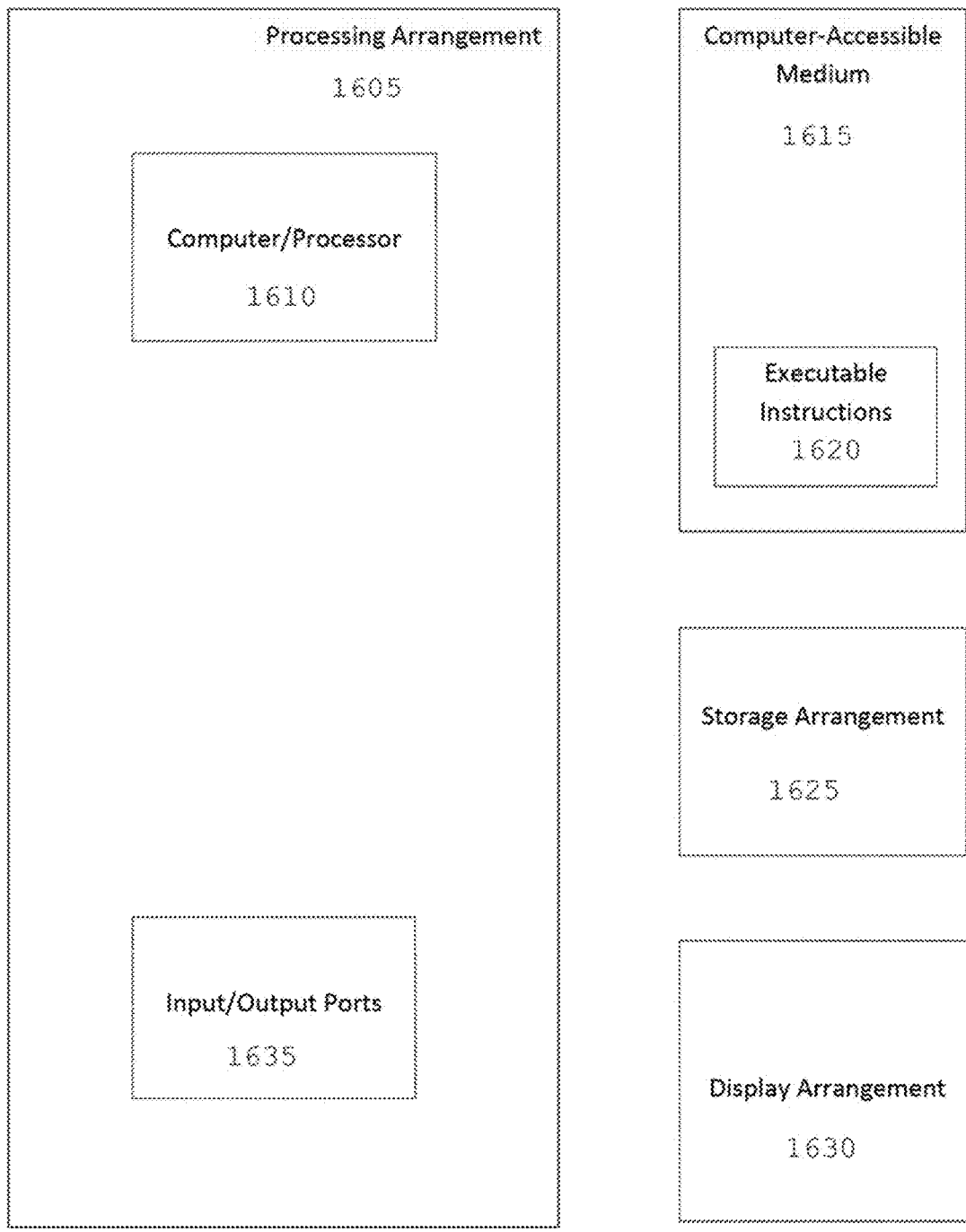
FIG. 16 is an illustration of an exemplary block diagram of an exemplary system in accordance with certain exemplary embodiments of the present disclosure.

FIG. 16 illustrates a block diagram of an exemplary embodiment of a system according to the present disclosure which can be programmed to perform the exemplary method shown in FIG. 15. For example, exemplary procedures in accordance with the present disclosure described herein can be performed by a processing arrangement and/or a computing arrangement 1605. Such processing/computing arrangement 1605 can be, for example entirely or a part of, or include, but not limited to, a computer/processor 1610 that can include, for example one or more microprocessors, and use instructions stored on a computer-accessible medium (e.g., RAM, ROM, hard drive, or other storage device).

As shown in FIG. 16, for example a computer-accessible medium 1615 (e.g., as described herein above, a storage device such as a hard disk, floppy disk, memory stick, CD-ROM, RAM, ROM, etc., or a collection thereof) can be provided (e.g., in communication with the processing arrangement 1605). The computer-accessible medium 1615 can contain executable instructions 1620 thereon. In addition or alternatively, a storage arrangement 1625 can be provided separately from the computer-accessible medium 1615, which can provide the instructions to the processing arrangement 1605 so as to configure the processing arrangement to execute certain exemplary procedures, processes and methods, as described herein above, for example.

Further, the exemplary processing arrangement 1605 can be provided with or include an input/output arrangement 1635, which can include, for example a wired network, a wireless network, the internet, an intranet, a data collection probe, a sensor, etc. As shown in FIG. 16, the exemplary processing arrangement 1605 can be in communication with an exemplary display arrangement 1630, which, according to certain exemplary embodiments of the present disclosure, can be a touch-screen configured for inputting information to the processing arrangement in addition to outputting information from the processing arrangement, for example. Further, the exemplary display 1630 and/or a storage arrangement 1625 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:

[1] Wedeen et al. Science 2012.
[2] Fernandez-Miranda et al. Neurosurgery 2012.
[3] Candes et al. J. ACM 2011.
[4] Otazo et al. Magn. Reson. Med. 2015.
[5] Baete, S. H., Magn. Reson. Med. 2015.
[6] Yeh, et al. NeuroImage 2015.
[7] Shen et al. Neuroimage 2016.
[8] Chen et al. HBM 2015.
[9] Wedeen, V. J., Science 2012.
[10] Fernandez-Miranda, J. C., Neurosurgery, 2012.
[11] Baete, S. H., ISMRM, 2015.
[12] Baete, S. H., Magn. Reson. Med., 2015.
[13] Yeh, F-C., NeuroImage, 2013.
[14] Yeh, F-C. NeuroImage, 2015.
[15] Jahanshad, N., Neurobiology of Aging, 2015.
[16] Chen, J. Human Brain Mapping, 2015.
[17] Candes, E. J., Journal of the ACM, 2011.
[18] Otazo, R., Magn. Reson. Med., 2015.
[19] Setsompop, K., NeuroImage, 2012.
[20] Klein, S, IEEE TMI, 2010.
[21] Yeh, F-C. IEEE TMI, 2010.
[22] Callaghan P. T. Principles of Nuclear Magnetic Resonance Microscopy. Oxford: Oxford University Press 1993.
[23] Basser P. J., Pierpaoli C. Microstructural and Physiological Features of Tissues Elucidated by Quantitative-Diffusion-Tensor Mill J Magn Reson Imaging Series B. 1996; 111:209-219.
[24] Tuch D. S., Reese T. G., Wiegell M. R., Makris N., Belliveau J. W., Wedeen V. J. High angular resolution diffusion imaging reveals intravoxel white matter fiber heterogeneity Magn Reson Med. 2002; 48:577-82.
[25] Wedeen V. J., Hagmann P., Tseng W. Y., Reese T. G., Weisskoff R. M. Mapping complex tissue architecture with diffusion spectrum magnetic resonance imaging Magn Reson Med. 2005; 54:1377-86.
[26] Wedeen V. J., Rosene D. L., Wang R., Dai G., Mortazavi F., Hagmann P., Kaas J. H., Tseng W. Y. The geometric structure of the brain fiber pathways Science. 2012; 335:1628-34.
[27] Reese T. G., Benner T., Wang R., Feinberg D. A., Wedeen V. J. Halving imaging time of whole brain diffusion spectrum imaging and diffusion tractography using simultaneous image refocusing in EPI J Magn Reson Imaging. 2009; 29:517-22.
[28] Tuch D. S. Q-ball imaging Magn Reson Med. 2004; 52:1358-72.
[29] Fernandez-Miranda J. C., Pathak S., Engh J., Jarbo K., Verstynen T., Yeh F. C., Wang Y., Mintz A., Boada F., Schneider W., Friedlander R. High-definition fiber tractography of the human brain: neuroanatomical validation and neurosurgical applications Neurosurgery. 2012; 71:430-53.

[30] Liu I.-C., Chiu C.-H., Chen C.-J., Kuo L. W., Lo Y.-C., Tseng W.-Y. I. The microstructural integrity of the corpus callosum and associated impulsivity in alcohol dependence: A tractography-based segmentation study using diffusion spectrum imaging Psychiatry Research: Neuroimaging. 2010; 184:128-34.

[31] Jarbo, K., Verstynen T., Schneider W. In vivo quantification of global connectivity in the human corpus callosum NeuroImage. 2012; 59:1988-96.

[32] Kuo L. W., Chen J. H., Wedeen V. J., Tseng W. Y. Optimization of diffusion spectrum imaging and q-ball imaging on clinical MRI system Neuroimage. 2008; 41:7-18.

[33] Setsompop K., Gagoski B. A., Polimeni J. R., Witzel T., Wedeen V. J., Wald L. L. Blipped-Controlled Aliasing in Parallel Imaging for Simultaneous Multislice Echo Planar Imaging With Reduced g-Factor Penalty Mag Reson Med. 2012; 67:1210-1224.

[34] Setsompop K., Cohen-Adad J., Gagoski B. A., Raij T., Yendiki A., Keil B., Wedeen V. J., Wald L. L. Improving diffusion MRI using simultaneous multi-slice echo planar imaging Neuroimage. 2012; 63:569-80.

[35] Blaimer M., Choli M., Jakob P. M., Griswold M. A., Breuer F. A. Multiband Phase-Constrained Parallel MRI Mag Reson Med. 2013; 69:974-980.

[36] Baete S., Zhao T., Boada F. E. Fast, whole brain Radial Diffusion Spectrum Imaging (RDSI) via Simultaneous Multi Slice Excitation in Proc Intl Soc Magn Reson Med; 23 (Toronto, Canada): 2539 2015.

[37] Baete S. H., Yutzy S., Boada F. Radial q-space sampling for DSI Magn Reson Med. 2016; 76:769-80.

[38] Baete S. H., Boada F. E. Accelerated Radial Diffusion Spectrum Imaging using a multi-echo stimulated echo diffusion sequence in Proc Intl Soc Magn Reson Med; 22 (Milan, Italy): 88 2014.

[39] Whitcher B., Wisco J. J., Hadjikhani N., Tuch D. S. Statistical Group Comparison of Diffusion Tensors Via Multivariate Hypothesis Testing Mag Reson Med. 2007; 57:1065-74.

[40] Smith S. M., Jenkinson M., Johansen-Berg H., Rueckert D., Nichols T. E., Mackay C. E., Watkins K. E., Ciccarelli O., Zaheer Cader M., Matthes P. M., Behrens T. E. Tract-based spatial statistics: Voxel-wise analysis of multi-subject diffusion data NeuroImage. 2006; 31:1487-1505.

[41] Jbabdi S., Behrens T. E., Smith S. M. Crossing fibres in tract-based spatial statistics NeuroImage. 2010; 46:249-56.

[42] Zhang H., Awate S. P., Das R. S., Woo J. H., Melhem E. R., Gee J. C., Yushkevich P. A. A tract-specific framework for white matter morphometry combining macroscopic and microscopic tract features Med Image Anal. 2010; 14:666-73.

[43] Jeurissen B., Leemans A., Tournier J.-D., Jones D. K., Sijbers J. Investigating the prevalence of complex fiber configurations in white matter tissue with diffusion magnetic resonance imaging Hum Brain Mapp. 2013; 34:2747-66.

[44] Bach M., Laun F. B., Leemans A., Tax C. M. W., Biessels G. J., Stieltjes B., Maier-Hein K. H. Methodological considerations on tract-based spatial statistics (TBSS) NeuroImage. 2014; 100:358-69.

[45] [24] Raffelt D. A., Smith R. E., Ridgway G. R., Tournier J.-D., Vaughan D. N., Rose S., Henderson R., Connelly A. Connectivity-based fixel enhancement: Whole-brain statistical analysis of diffusion MRI measures in the presence of crossing fibres NeuroImage. 2015; 117:40-55.

[46] Jahanshad N., Nir T. M., Toga A. W., Jack C. R. Jr, Bernstein M. A., Weiner M. W., Thompson P. M. Seemingly unrelated regression empowers detection of network failure in dementia Neurobiology of Aging. 2015; 36:S103-12.

[47] Chen J., Baete S., Qian M., Li M., Marmar C., Boada F. E. Principle Component Analysis of Orientation Distribution Function in Diffusion Spectrum Imaging in Human Brain Mapping; 21 (Honolulu, Hi.):5126 2015.

[48] Raffelt D., Tournier J.-D., Rose S., Ridgway G. R., Henderson R., Crozier S., Salvado O., Connelly A. Apparent Fibre Density: A novel measure for the analysis of diffusion-weighted magnetic resonance images NeuroImage. 2012; 59:3976-94.

[49] Yeh F.-C., Badre D., Verstynen T. Connectome-try: A statistical approach harnessing the analytical potential of the local connectome NeuroImage. 2016; 125:162-71.

[50] Mitra J., Shen K., Ghose S., Bourgeat P., Fripp J., Salvado O., Pannek K., Taylor D. J., Mathias J. L., Rose S. Statistical machine learning to identify brain injury (TBI) from structural disconnections of white matter networks NeuroImage. 2016; 129:247-59.

[51] Smith S. M., Nichols T. E. Threshold-free cluster enhancement: Addressing problems of smoothing, threshold dependence and localisation in cluster inference NeuroImage. 2009; 44:83-98.

[52] Jones D. K., Knosche T. R., Turner R. White matter integrity, fiber count, and other fallacies: The do's and don'ts of diffusion MRI NeuroImage. 2013; 73:239-254.

[53] Reveley C., Seth A. K., Pierpaoli C., Silva A. C., Yu D., Saunders R. C., Leopold D. A., Ye F. Q. Superficial white matter fiber systems impede detection of long-range cortical connections in diffusion MR tractography Proc Natl Acad Sci USA. 2015; 112:E2820-8.

[54] Thomas C., Ye F. Q., Irfanoglu M. O., Modi P., Saleem K. S., Leopold D. A., Pierpaoli C. Anatomical accuracy of brain connections derived from diffusion MRI tractography is inherently limited Proc Natl Acad Sci USA. 2014; 111:16574-9.

[55] Lepore N., Brun C., Descoteaux M., Chou Y.-Y., Zubicaray G., McMahon K., Wright M. J., Martin N. G., Gee J. C., Thompson P. M. A Multivariate Group-wise Genetic Analysis of White Matter Integrity using Orientation Distribution Functions in Computational Diffusion MRI workshop at MICCAI(Beijing, China) 2010.

[56] Zhou X., Yang C., Zhao H., Yu W. Low-Rank Modeling and its Applications in Image Analysis arXiv preprint. 2014; arXiv:1401.3409.

[57] Lin Z. A review on low-rank models in data analysis Big Data and Inf. Anal. 2016; epub ahead of print: DOI:10.3934/bdia.2016001.

[58] Candes E. J., Li X., Ma Y., Wright J. Robust Principal Component Analysis? Journal of the ACM. 2011; 58:11.

[59] Chandrasekaran V., Sanghavi S., Parrilo P. A., Willsky A. S. Rank-Sparsity incoherence for matrix decomposition SIAM J. Optim. 2011; 21:572-96.

[60] Otazo R., Candes E. J., Sodickson D. K. Low-Rank Plus Sparse Matrix Decomposition for Accelerated Dynamic MRI with Separation of Background and Dynamic Components Mag Reson Med. 2015; 73:1125-36.

[61] Yeh F. C., Wedeen V. J., Tseng W. Y. Generalized q-Sampling Imaging IEEE Trans Med Imaging. 2010; 29:1626-35.

[62] Tournier J.-D., Calamante F., Gadian D. G., Connelly A. Direct estimation of the fiber orientation density function from diffusion-weighted MRI data using spherical deconvolution NeuroImage. 2004; 23:1176-85.
[63] Peng Y., Ganesh A., Wright J., Xu W., Ma Y. RASL: Robust Alignment by Sparse and Low-Rank Decomposition for Linearly Correlated Images IEEE Trans Pattern Anal. and Mach. Int. 2012; 34:2233-46.
[64] Bouwmans T., ZahZah E. H. Robust PCA via Principal Component Pursuit: A review for a comparative evaluation in video surveillance Comp. Vis. and Imag. Understanding. 2014; 122:22-34.
[65] Gao H., Li L., Hyu X. Compressive Diffusion MRI-Part 1: Why Low-Rank? in Proc Intl Soc Magn Reson; 21 (Salt Lake City, Utah, USA):610 2013.
[66] Gao H., Cai J.-F., Shen Z., Zhao H. Robust principal component analysis-based four-dimensional computed tomography Phys. Med. Biol. 2011; 56:3181-98.
[67] Otazo R., Franco A., Chen J., Marmar C., Boada F. Low-rank plus sparse (L+S) decomposition for separation of subsampled physiological noise in fMRI in Human Brain Mapping; 21 (Honolulu, Hi., USA):1690 2015.
[68] Yuan X., Yang J. Sparse and Low-Rank Matrix Decomposition Via Alternating Direction Methods Optimization Online. November 2009.
[69] Lin Z., Chen M., Ma Y. The Augmented Lagrange Multiplier Method for Exact Recovery of Corrupted Low-Rank Matrices arXiv preprint. 2010:arXiv:1009.5055v3.
[70] Nichols T. E., Holmes A. P. Nonparametric Permutation Tests For Functional Neuroimaging: A Primer with Examples Hum Brain Mapp. 2001; 15:1-25.
[71] Winkler A. M., Ridgway G. R., Webster M. A., Smith S. M., Nichols T. E. Permutation inference for the general linear modal NeuroImage. 2014; 92:381-97.
[72] Cohen-Adad J., Descoteaux M., Wald L. L. Quality assessment of high angular resolution diffusion imaging data using bootstrap on Q-ball reconstruction J Magn Reson Imaging. 2011; 33:1194-208.

What is claimed is:

1. A non-transitory computer-accessible medium having stored thereon computer-executable instructions for determining at least one difference between at least two sets of subjects, wherein, when a computer arrangement executes the instructions, the computer arrangement is configured to perform procedures comprising:
receiving first imaging information related to at least one first set of subjects of the at least two sets of the subjects;
receiving second imaging information related to at least one second set of subjects of the at least two sets of subjects;
generating at least one first matrix based on the first imaging information and at least one second matrix based on the second imaging information, wherein columns of the at least one first matrix correspond to particular first subjects in the at least one first set of subjects, and rows of the at least one first matrix correspond to features of the particular first subjects, and wherein columns of the at least one second matrix correspond to particular second subjects in the at least one second set of subjects, and rows of the at least one second matrix correspond to features of the particular second subjects;
generating third information by performing at least one low rank plus sparse (L+S) decomposition procedure on the at least one first matrix and the at least one second matrix; and
determining the at least one difference based on the third information.

2. The computer-accessible medium of claim 1, wherein:
the first imaging information includes a plurality of first images, and wherein a particular image of the first images corresponds to a particular first subject in the at least one first set of subjects, and
the second imaging information includes a plurality of second images, and wherein a particular image of the second images corresponds to a particular second subject in the at least one second set of subjects.

3. The computer-accessible medium of claim 1, wherein the at least one first set of subjects is different than the at least one second set of subjects.

4. The computer-accessible medium of claim 1, wherein the computer arrangement is configured to generate the third information by decomposing (i) the at least one first matrix into at least one first low-rank matrix and at least one first residual matrix using the L+S decomposition procedure, and (ii) the at least one second matrix into at least one second low-rank matrix and at least one second residual matrix using the L+S decomposition procedure.

5. The computer-accessible medium of claim 4, wherein the computer arrangement is configured to determine the at least one difference based on the at least one first low-rank matrix and the at least one second low-rank matrix.

6. The computer-accessible medium of claim 5, wherein the computer arrangement is configured to determine the at least one difference by comparing the at least one first low-rank matrix to the at least one second low-rank matrix on a voxel by voxel basis.

7. The computer-accessible medium of claim 4, wherein the at least one first residual matrix includes outliers from the at least one first set of subjects and the at least one second residual matrix includes outliers from the at least one second set of subjects.

8. The computer-accessible medium of claim 1, wherein the computer arrangement is further configured to co-register the first information and the second imaging information.

9. The computer-accessible medium of claim 8, wherein the computer arrangement is further configured to map the first imaging information and the second imaging information to at least one atlas.

10. The computer-accessible medium of claim 1, wherein the computer arrangement is further configured to generate the first imaging information and the second imaging information.

11. The computer-accessible medium of claim 1, wherein the first imaging information and the second imaging information include at least one of magnetic resonance imaging information, computed tomography imaging information, optical coherence tomography imaging information, ultrasound imaging information or Optical Frequency Domain Reflectometry imaging information.

12. The computer-accessible medium of claim 1, wherein the first imaging information includes a plurality of first images of brains of the at least one first set of subjects, and the second imaging information includes a plurality of second images of brains of the at least one second set of subjects.

13. The computer-accessible medium of claim 12, wherein the at least one difference includes a presence or absence of a traumatic brain injury.

14. The computer-accessible medium of claim 1, wherein the at least one difference includes an Orientation Distribution Function group difference.

15. A method for determining at least one difference between at least two sets of subjects, comprising:

receiving first imaging information related to at least one first set of subjects of the at least two sets of subjects;

receiving second imaging information related to at least one second set of subjects of the at least two sets of subjects;

generating at least one first matrix based on the first imaging information and at least one second matrix based on the second imaging information, wherein columns of the at least one first matrix correspond to particular first subjects in the at least one first set of subjects, and rows of the at least one first matrix correspond to features of the particular first subjects, and wherein columns of the at least one second matrix correspond to particular second subjects in the at least one second set of subjects, and rows of the at least one second matrix correspond to features of the particular second subjects;

generating third information by performing at least one low rank plus sparse (L+S) decomposition procedure on the at least one first matrix and the at least one second matrix; and using a specifically configured computer hardware arrangement, determining the at least one difference based on the third information.

16. A system for determining at least one difference between at least two sets of subjects, comprising:

a computer hardware arrangement specifically configured to:

receive first imaging information related to at least one first set of subjects of the at least two sets of subjects;

receive second imaging information related to at least one second set of subjects of the at least two sets of subjects;

generate at least one first matrix based on the first imaging information and at least one second matrix based on the second imaging information, wherein columns of the at least one first matrix correspond to particular first subjects in the at least one first set of subjects, and rows of the at least one first matrix correspond to features of the particular first subjects, and wherein columns of the at least one second matrix correspond to particular second subjects in the at least one second set of subjects, and rows of the at least one second matrix correspond to features of the particular second subjects;

generate third information by performing at least one low rank plus sparse (L+S) decomposition procedure on the at least one first matrix and the at least one second matrix; and determine the at least one difference based on the third information.

* * * * *

UNITED STATES PATENT AND TRADEMARK OFFICE
CERTIFICATE OF CORRECTION

| | | |
|---|---|---|
| PATENT NO. | : 10,307,139 B2 | Page 1 of 1 |
| APPLICATION NO. | : 15/419508 | |
| DATED | : June 4, 2019 | |
| INVENTOR(S) | : Fernando Boada et al. | |

It is certified that error appears in the above-identified patent and that said Letters Patent is hereby corrected as shown below:

In the Specification

Please amend the second paragraph under Column 1, Line 6 with the following paragraph:
STATEMENT AS TO FEDERALLY SPONSORED RESEARCH
This invention was made with government support under Grant Nos. R01CA111996, R01NS082436 and R01 MH00380, awarded by the National Institute of Health. The government has certain rights in the invention Signed and Sealed this
Twenty-second Day of April, 2025

Coke Morgan Stewart
*Acting Director of the United States Patent and Trademark Office*